(12) United States Patent
Kubinski

(10) Patent No.: US 10,364,717 B2
(45) Date of Patent: Jul. 30, 2019

(54) METHODS AND SYSTEMS FOR INCREASING PARTICULATE MATTER DEPOSITION IN AN EXHAUST PARTICULATE MATTER SENSOR

(71) Applicant: Ford Global Technologies, LLC, Dearborn, MI (US)

(72) Inventor: David John Kubinski, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 134 days.

(21) Appl. No.: 15/698,857

(22) Filed: Sep. 8, 2017

(65) Prior Publication Data

US 2018/0023431 A1  Jan. 25, 2018

Related U.S. Application Data

(62) Division of application No. 14/613,012, filed on Feb. 3, 2015, now Pat. No. 9,803,524.

(51) Int. Cl.
*F01N 3/027* (2006.01)
*G01N 15/00* (2006.01)
*G01N 15/06* (2006.01)

(52) U.S. Cl.
CPC ......... *F01N 3/027* (2013.01); *G01N 15/0656* (2013.01); *G01N 2015/0046* (2013.01)

(58) Field of Classification Search
CPC .............. F01N 3/027; G01N 15/0656; G01N 2015/0046
See application file for complete search history.

(56) References Cited

U.S. PATENT DOCUMENTS

| 7,543,477 B2 | 6/2009 | Berger et al. |
| 8,035,404 B2 | 10/2011 | Schnell et al. |
| 8,310,249 B2 | 11/2012 | Paterson |
| (Continued) | | |

FOREIGN PATENT DOCUMENTS

| CN | 103688161 A | 3/2014 |
| CN | 104880393 A | 9/2015 |
| WO | 03006976 A2 | 1/2003 |

OTHER PUBLICATIONS

Van Gerwen, P. et al., "Nanoscaled interdigitated electrode arrays for biochemical sensors," Sensors and Actuators B, vol. 49, No. 1-2, Jun. 1998, 8 pages.

(Continued)

*Primary Examiner* — Brandon D Lee
(74) *Attorney, Agent, or Firm* — Julia Voutyras; McCoy Russell LLP

(57) ABSTRACT

Methods are described for increasing the sensitivity of particulate matter detection in an exhaust system of a vehicle. An example particulate matter sensor assembly comprises a pair of planar interdigitated electrode structures held at a voltage bias with respect to each other. An alternate embodiment may comprise a planar interdigitated electrode pair, and a conducting plate assembly again held at a voltage bias with respect to the planar interdigitated electrode pair. The bias may overlay an additional electric field drive, which improves the capture of soot particles on the sensor assembly surface thereby increasing sensitivity of particulate matter sensors.

8 Claims, 10 Drawing Sheets

(56) References Cited

U.S. PATENT DOCUMENTS

| | | |
|---|---|---|
| 8,823,401 B2 | 9/2014 | Roth et al. |
| 2011/0192211 A1 | 8/2011 | Yokoi et al. |
| 2012/0151992 A1* | 6/2012 | Harada .............. G01N 15/0656 |
| | | 73/23.33 |
| 2017/0299490 A1* | 10/2017 | Tiefenbach ........ G01N 15/0606 |

OTHER PUBLICATIONS

Green, N. et al., "Numerical solution of the dielectrophoretic and travelling wave forces for interdigitated electrode arrays using the finite element method," Journal of Electrostatics, vol. 56, No. 2, Sep. 2002, 20 pages.

Mamishev, A. et al., "Interdigital Sensors and Transducers," Proceedings of the 2004 IEEE, vol. 92, No. 5, May 2004, 38 pages.

State Intellectual Property Office of the People's Republic of China, Office Action and Search Report Issued in Application No. 201610076928.7, dated May 27, 2019, 9 pages. (Submitted with Partial Translation).

* cited by examiner

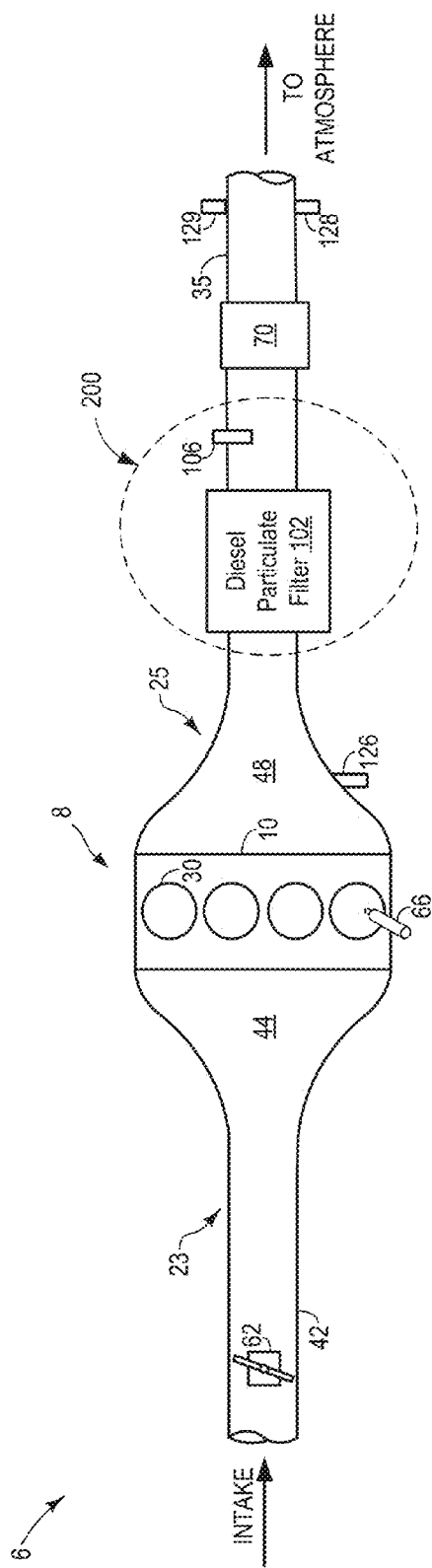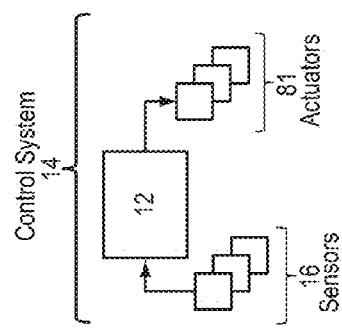
FIG. 1

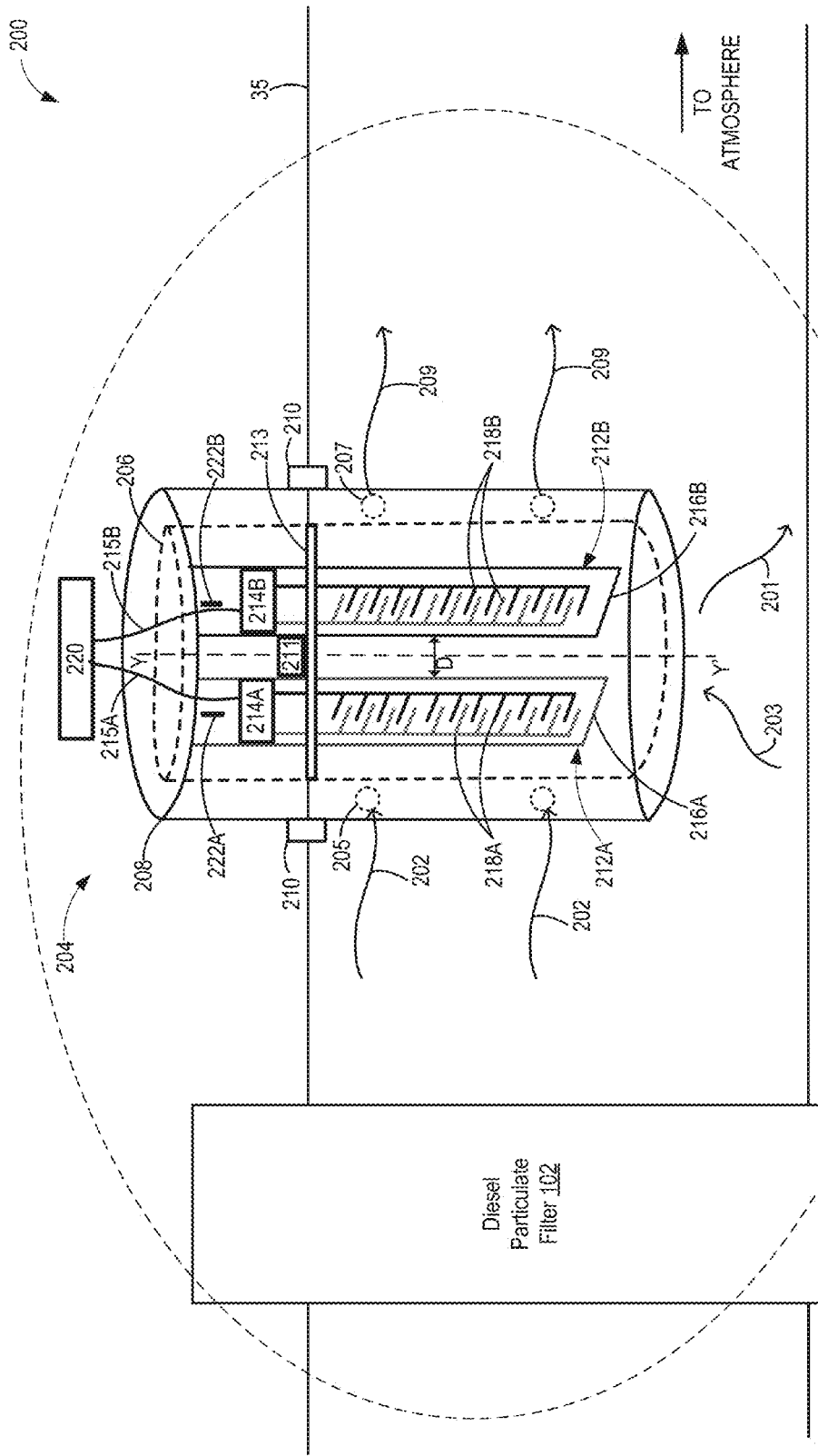

METHODS AND SYSTEMS FOR INCREASING PARTICULATE MATTER DEPOSITION IN AN EXHAUST PARTICULATE MATTER SENSOR

CROSS REFERENCE TO RELATED APPLICATION

The present application is a divisional of U.S. patent application Ser. No. 14/613,012, entitled "METHODS AND SYSTEMS FOR INCREASING PARTICULATE MATTER DEPOSITION IN AN EXHAUST PARTICULATE MATTER SENSOR," filed on Feb. 3, 2015. The entire contents of the above-referenced application are hereby incorporated by reference in its entirety for all purposes.

FIELD

The present description relates generally to the design and use of resistive-type particle matter (PM) sensors in an exhaust gas flow.

BACKGROUND/SUMMARY

Diesel combustion exhaust is a regulated emission. Diesel particulate matter (PM), is the particulate component of diesel exhaust, which includes diesel soot and aerosols such as ash particulates, metallic abrasion particles, sulfates, and silicates. When released into the atmosphere, PMs can take the form of individual particles or chain aggregates, with most in the invisible sub-micrometer range of 100 nanometers. Various technologies have been developed for identifying and filtering out exhaust PMs before the exhaust is released to the atmosphere.

As an example, soot sensors, also known as PM sensors, may be used in vehicles having internal combustion engines. A PM sensor may be located upstream and/or downstream of a diesel particulate filter (DPF), and may be used to sense PM loading on the filter and diagnose operation of the particulate filter. Typically, a resistive PM sensor may sense a soot level based on a correlation between a measured change in electrical conductivity (or resistivity) between a pair of electrodes placed on a planar substrate surface of the sensor with the amount of PM deposited between the measuring electrodes. Specifically, the measured conductivity provides a measure of soot accumulation because the PM is composed primarily of electrically conductive carbon soot, with a smaller fraction of lower conductivity components such as volatile organics and metal oxides (oil ash).

One example PM sensor design is shown by Roth et al. in U.S. Pat. No. 8,823,401B2. Therein, a pair of planar adjacently placed interdigitated electrodes, either placed with a gap between them or juxtaposed together, connected to a common voltage source are used to independently detect PMs in the exhaust. As the PMs deposit on the interdigitated electrode pair due to electrostatic attraction between the charged PMs and the electrodes, the output of the two independent PM sensors are further analyzed and compared using extensive algorithms to derive meaningful information about the amount of PMs in the exhaust.

However, the inventors herein have recognized potential issues with such an approach. The PM sensors described by Roth et al. may continue to have reduced sensitivity due to the poor electrostatic attraction experienced by the PMs located away from the sensor surface in the electric field generated by the electrode pair. While the strength of the electric field in the region between each planar interdigitated electrode pair is higher near the surface of the electrode pair, the electric field decays rapidly away from it. Additionally, the sensor output of Roth et al., requires analysis with extensive algorithms to derive meaningful information regarding PM in the exhaust, leading to extended processing times and undesired delays in data output and diagnostics.

The inventors have identified an approach to partly address these issues while improving the sensitivity of the PM sensors. In one example approach, PM sensor reliability may be improved by a method comprising of generating a first electric field via a planar interdigitated electrode pair and generating a second electric field via the planar interdigitated electrode pair and a second planar element parallel with the planar interdigitated electrode pair. As a result, the strength of the electric field generated in the region between the two interdigitated electrode pairs which is normal to the surface of the interdigitated electrode pairs, can be increased, thereby increasing the electrostatic attraction of the PMs and increasing sensitivity of the PM sensors.

As an example, the PM sensor assembly could comprise of a planar interdigitated electrode pair and a conducting plate which is held at a voltage bias compared to the electrode pair; in an alternate embodiment, the conducting plate could be replaced by a second planar interdigitated electrode pair, again held at a voltage bias with respect to the first interdigitated electrode pair, such that there is an additional electric field created normal to the surface of the PM sensors. The technical effect of using such a PM sensor assembly to detect exhaust soot is that, the additional electric field between the conducting plate (or the second planar interdigitated electrode pair) and the first planar interdigitated electrode pair increases the electrostatic attraction thereby increasing the amount of soot that gets deposited on the PM sensor, thereby improving sensitivity of the PM sensor assembly to the detection of soot. Further, by increasing the voltage bias, the electric field strength may be increased. In one example configuration, where the two PM sensors face each other, the sensitivity of each PM sensor in the assembly may be increased by increasing the voltage bias. By using the collective output of both the sensors, a more accurate measure of the exhaust soot load, and thereby the DPF soot load can be determined. In addition, the increased sensitivity of the PM sensor allows for the rapid detection of PMs leaking downstream of a degraded DPF. As such, this improves the efficiency of filter regeneration operations, and reduces the need for extensive algorithms. In addition, by enabling more accurate diagnosis of an exhaust DPF, exhaust emissions compliance may be improved.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 1 shows a schematic diagram of an engine and an associated resistive-based exhaust particulate matter (PM) sensor.

FIG. 2 shows a schematic diagram of the PM sensor assembly of FIG. 1 with a pair of sensors separated by a distance.

DETAILED DESCRIPTION

Figure 3B:
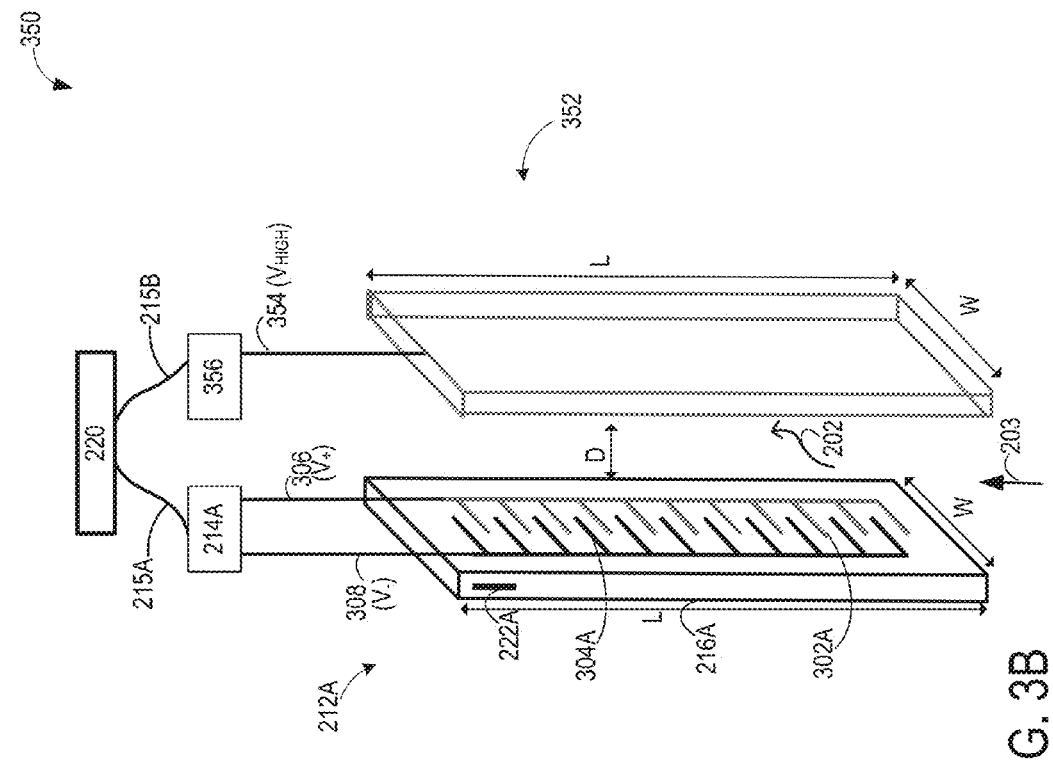
FIGS. 3A-B show exploded views of two example embodiments of the PM sensor assembly of FIG. 1.
Figure 4:
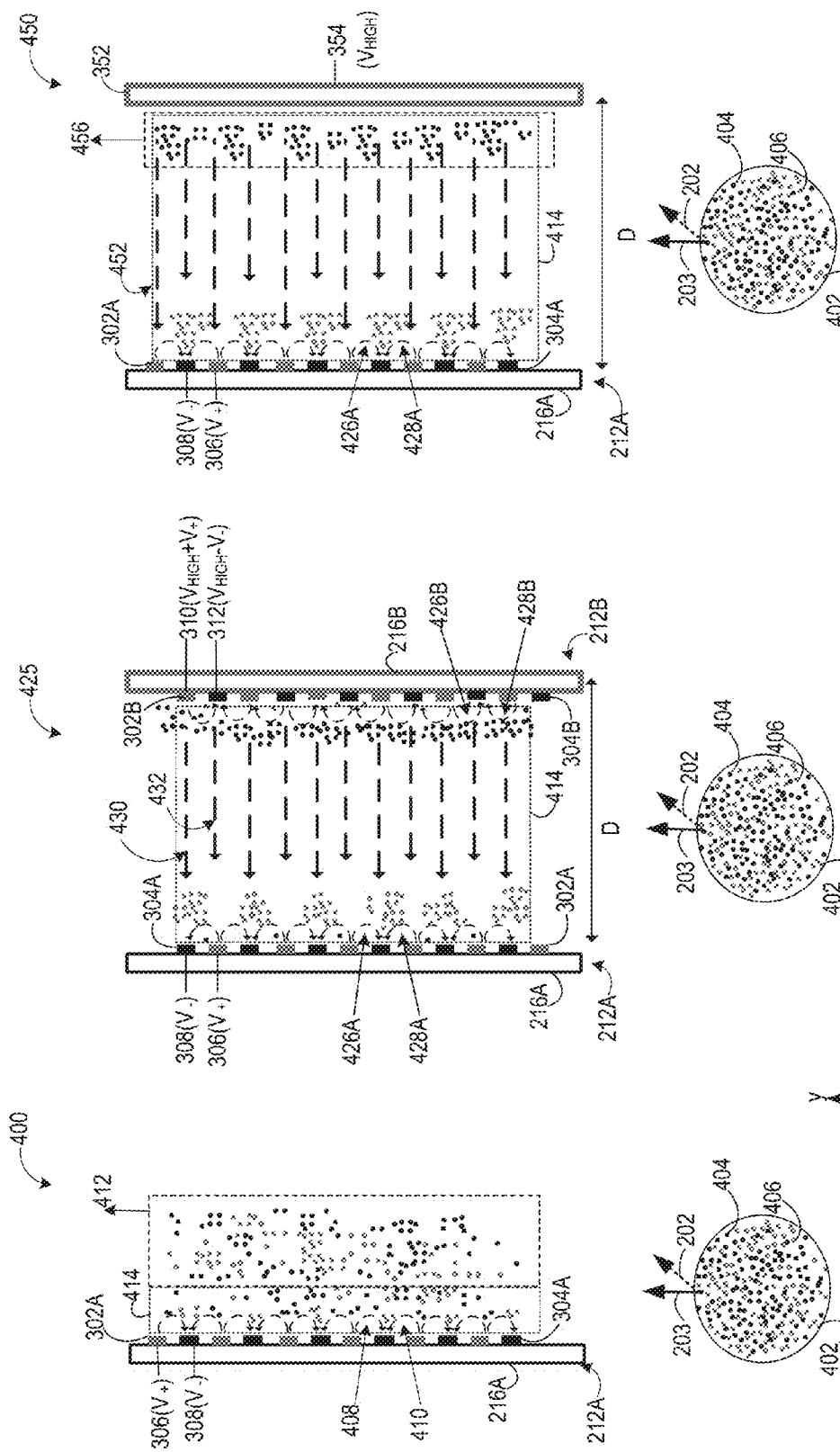
FIG. 4 shows electric field lines generated in the example PM assembly embodiments of FIG. 3.
Figure 5:
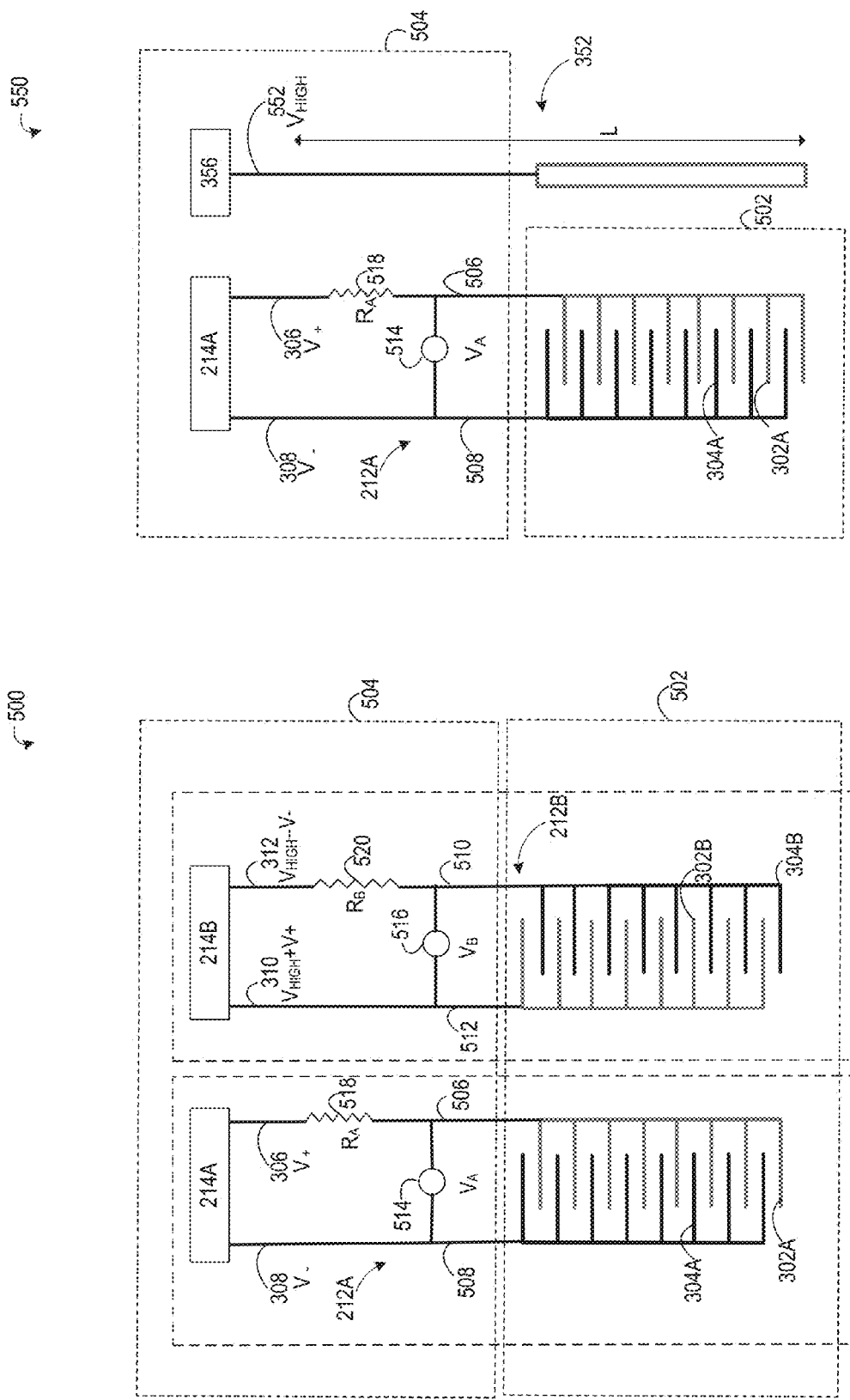
FIG. 5 shows circuit diagrams for the example PM assembly embodiments, according to the present disclosure.
Figure 8:
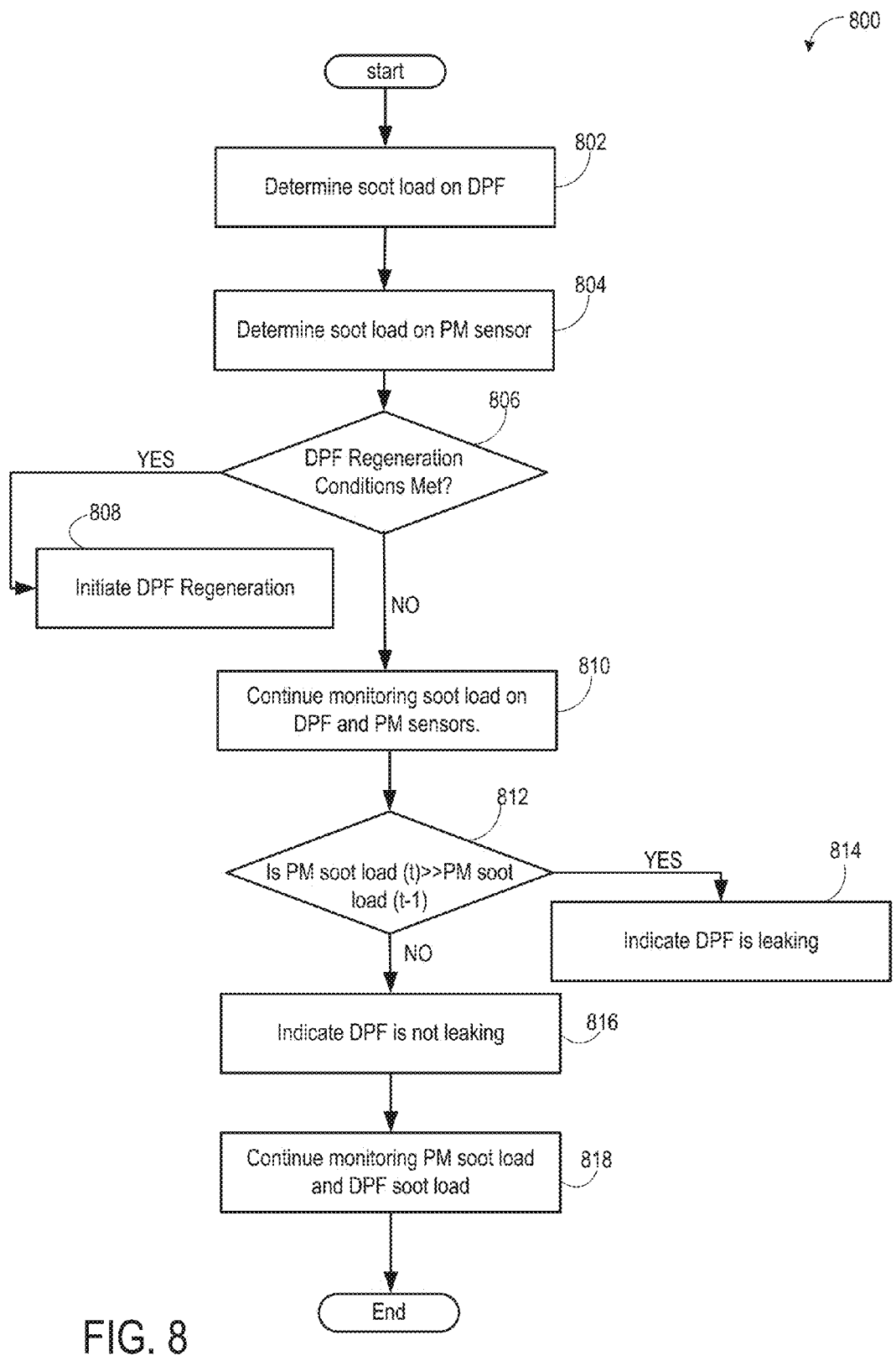
FIG. 8 shows a high level flow chart that may be implemented for diagnosing particulate filter regeneration and functionality, using the PM sensor assembly embodiments, according to the present disclosure.
Figure 9:
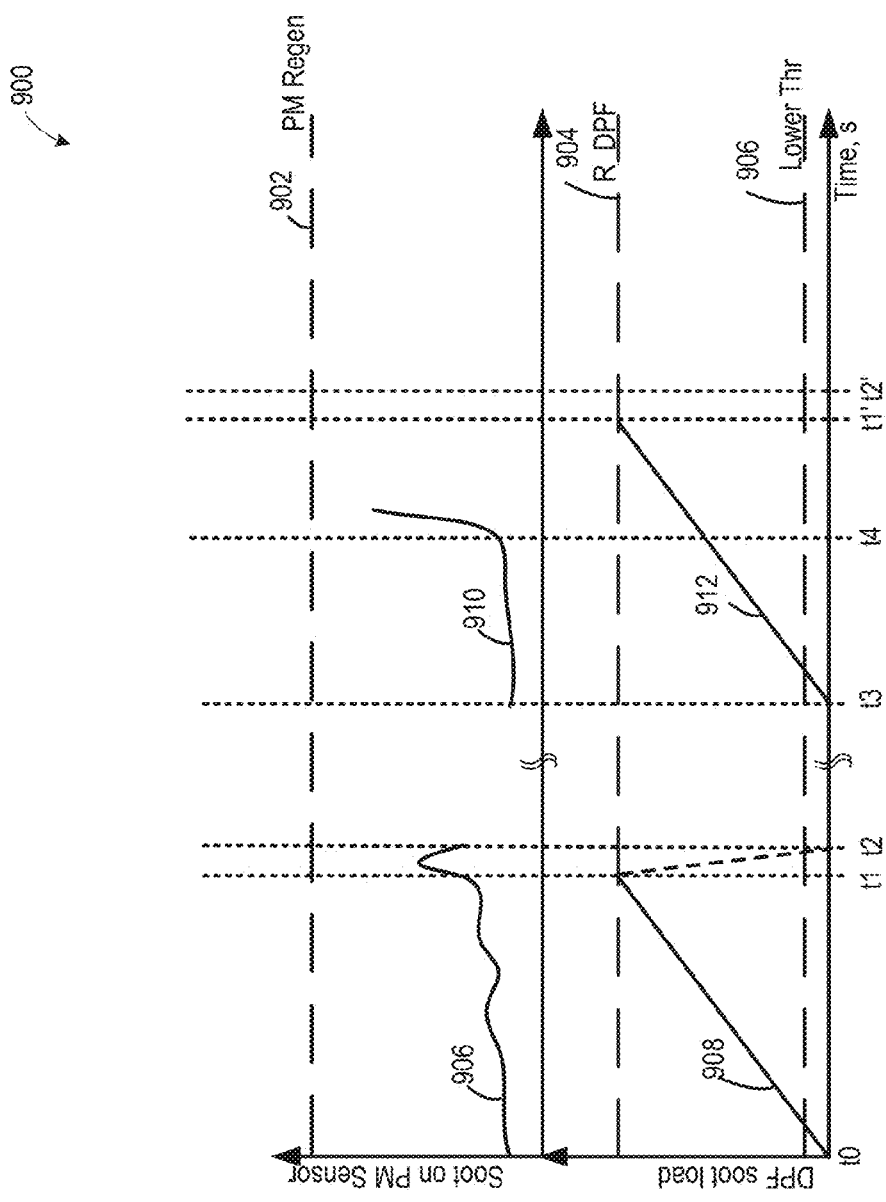
FIG. 9 shows an example relationship between soot detected by PM sensor and soot load on particulate filter

The following description relates to systems and methods for measuring the amount of particulate matter stored on an engine exhaust particulate filter, such as in the vehicle system of FIG. 1. A particulate matter (PM) sensor configured with a pair of electrodes separated by a gap (FIGS. 2-3) may be located downstream or upstream of the diesel particulate filter. The electrodes may be operated with a voltage bias relative to one another to increase the electrostatic force applied on exhaust soot particles, thereby improving soot accumulation on the sensors (FIGS. 4-5). A controller may be configured to perform a control routine, such as the routine of FIG. 6 to regenerate the particulate filter based on an output of a pressure sensor and perform diagnostics on the particulate filter based on an output of the PM sensor (FIG. 9). In addition, the controller may intermittently clean the PM sensor (FIG. 7) to enable continued PM monitoring. The functioning of the particulate filter based on the output from a PM sensor placed downstream of the filter is shown in FIG. 8 and an example of filter diagnostics is shown in FIG. 9. An example relation between sensor output and filter regeneration is depicted with reference to FIG. 10. In this way, PM sensor sensitivity is increased and exhaust emissions compliance is improved.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PMs, following passage through DPF 102, may be measured in the PM sensor 106 and further processed in emission control device 70 and expelled to the atmosphere via exhaust passage 35. In the depicted example, PM sensor assembly 106 is a resistive sensor that estimates a soot load of DPF 102 based on a change in conductivity measured across the electrodes of the PM sensor. A schematic view 200 of the PM sensor assembly 106 is shown at FIG. 2. A detailed explanation of the operation of the PM sensor is provided with reference to FIG. 4.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust gas sensor 126 (located in exhaust manifold 48), temperature sensor 128, pressure sensor 129 (located downstream of emission control device 70), and PM sensor assembly 106. Other sensors such as additional pressure, temperature, air/fuel ratio, and composition sensors may be coupled to various locations in the vehicle system 6. As another example, the actuators may include fuel injectors 66, throttle 62, DPF valves that control filter regeneration (not shown), etc. The control system 14 may include a controller 12. The controller may be configured with computer readable instructions stored on non-transitory memory. The controller may receive input data from the various sensors, process the input data, and trigger the actuators in response to the processed input data based on instruction or code programmed therein corresponding to one or more routines. Example routines are described herein with reference to FIGS. 6-7.

Turning now to FIG. 2, a schematic view 200 of an example embodiment of a particulate matter (PM) sensor assembly 204 is shown. In one example, PM sensor assembly 204 may be the PM sensor 106 of FIG. 1. PM sensor assembly 204 may be configured to measure PM mass and/or concentration in the exhaust gas, and as such, may be coupled to an exhaust passage (e.g., such as exhaust passage 35 shown in FIG. 1), upstream or downstream of a diesel particulate filter.

Schematic view 200 shows PM sensor assembly 204 inside exhaust passage 35 with exhaust gases flowing from downstream of a diesel particulate filter towards an exhaust tailpipe, as indicated by arrow 202. PM sensor assembly 204 may comprise a cylindrical tube 208 with an inner hollow section 206 (protection tube) that may serve to protect the electrical sensing elements of the sensor that are housed within and additionally may serve to redirect and optimize the gas flow over them. A plurality of holes 205, 207 (or pores) may be configured along the surface of cylindrical tube 208 for enabling flow-through of exhaust gas. Exhaust gas may enter the PM sensor assembly 204 through the plurality of holes 205 (two holes shown as a non-limiting example) on the upstream side of the cylindrical tube 208 closer to the DPF 102 as indicated by arrow 202. The exhaust may then flow between the two PM sensors 212A and 212B where the PMs may be detected, and the undetected PMs in the exhaust may exit the PM sensor assembly 204 on the downstream side, indicated by arrow 209, though plurality of holes 207 (two holes shown as a non-limiting example). Additionally, exhaust gas may enter and exit the PM sensor assembly 204 though the base of the cylindrical tube 208 that is positioned inside the exhaust passage 35 as indicated by arrows 203 and 201. In this way, exhaust gas may enter the cylindrical tube in a direction substantially parallel to the direction of exhaust flow as well as a perpendicular direction. The cylindrical tube 208 of the PM sensor assembly 204 may be mounted directly onto exhaust passage 35 such that the central axis Y-Y' may be perpendicular to the direction of exhaust flow as indicated by arrow 202. The portion of the sensor body that attaches to the exhaust pipe typically may have a screw thread 210 of larger diameter than the cylindrical tube 208 and may be concentric with it. This sensor mounting screw thread 210 may be screwed directly into a mounting base which is typically welded on to the exhaust pipe. This sort of sensor mounting is similar to that used for other automotive sensors (oxygen, NOx and temperature). The hollow section 206 of the PM sensor assembly 204 defines an enclosed volume within which sensor electrodes are housed.

The PM sensor assembly 204 may further include a pair of planar interdigitated electrode pairs, also known as PM sensors, 212A and 212B. The mounting attachments may comprise of one or more electrically insulating ceramic spacers 211 placed between the PM sensors 212A and 212B to ensure a separation of distance D between them as shown in FIG. 2. This spacer 211 may be held in place by a glass seal 213 located near the spacer 211. Other methods of holding the elements in place may also be used and are not the focus of this invention. The first PM sensor 212A within the PM sensor assembly 204 may be configured with a substrate 216A, a pair of interdigitated electrodes (also called sensing electrodes) 218A, a heating element 222A, connection pads 214A and connecting wiring 215A that connects the sensor 212A through the connection pads 214A to the external control module (ECM) 220. The external control module 220 houses the electronics and software and is located outside the exhaust passage (typically <1 meter away). In addition, the external control module may be communicatively coupled to an engine controller, such as controller 12 of FIG. 1, so that PM data collected at the sensor can be communicated with controller 12.

The substrate 216A of the PM sensor assembly 212A may be typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes 218A. The pair of planar interdigitated electrodes 218A of the PM sensor 212A may contain individual electrodes forming a "comb" structure indicated by black and grey lines in 218A. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. Each electrode of the pair of sensing electrodes 218A may be composed of the same or different material as the other sensing electrode of the pair. The comb structure of the interdigitated electrodes may cover the portion of the planar substrate 216A which is within the gas flow portioned out by the protection tube 206. The spacing between the comb "tines" of the two electrodes may typically be in the range from 10 micrometers to 100 micrometers with the linewidth of each individual "tine" being about the same value, although the latter is not necessary. The pair of interdigitated electrodes may be connected via electrical connections to the connection pad 214A. Connecting wiring 215A connects the electrodes 218A of the PM sensor 212A through the connection pad 214A to the appropriate terminals of a voltage supply in the external control module 220, the details of which are explained in FIG. 3. The external control module 220 may, in addition, contain circuitry responsible for detecting the changes in the electrical resistance across the pair of interdigitated electrodes 218A as PMs in the exhaust get deposited between the electrode pair 218A, and communicating these changes to an on-board controller, which are explained in detail in FIG. 5.

PM sensor 212A may comprise of a heating element 222A that may be integrated into the sensor substrate 216A. The heating element 222A may comprise, but is not limited to, a temperature sensor, and a heater, both together shown here as 222A. Possible materials for the heater and the temperature sensor forming the heating element 222A may include platinum, gold, palladium, and the like; and alloys, oxides, and combinations comprising at least one of the foregoing materials, with platinum/alumina, platinum/palladium, platinum, and palladium. The heating element 222A may be used for regenerating the PM sensor 212A. Specifically, during conditions when the soot load of the sensor is higher than a threshold, heating element 222A may be operated to burn accumulated soot particle from the surface of sensor 212A. During the regeneration, the external control module 220 may provide the voltage needed for operating the heating element 222A. By intermittently regenerating the PM sensor 212A, it may be returned to a condition more suitable for collecting exhaust soot. In addition, accurate information pertaining to the exhaust soot level may be inferred from the sensor regeneration and relayed to the controller.

The PM sensor assembly 204 may contain a second PM sensor 212B having the same configuration as first PM sensor 212A. That is, PM sensor 212B may be configured with substrate 216B, a planar interdigitated electrode pair 218B, heating element 222B, connection pads 214B, connecting wiring 215B connecting the PM sensor 212B to the external control module 220. As such, the details of each of the components of second PM sensor 212B may be similar to the corresponding components of PM sensor 212A described above. In one embodiment, the PM sensor assembly 204 may have the two PM sensors 212A and 212B described above facing each other and separated by a ceramic spacer 211 with a distance D between them. The PM sensors 212A and 212B may be mounted such that the exhaust gas entering the PM assembly 204 through holes 205 may flow parallel to the shorter edge of the substrates 216A and 216B. Alternately, the exhaust flow may enter and exit the PM sensor assembly 204 though the base of the cylindrical tube 208, parallel to the longer edge of the substrates 216A and 216B as indicated by arrows 203 and 201 respectively. In either case, the mechanism that the PM sensor assembly 204 uses to detect the PMs in the exhaust remain the same. The details of this embodiment with two PM sensors 212A and 212B are explained in FIG. 3A. In an alternate embodiment, one of the two PM sensors of the PM sensor assembly 204, such as PM sensor 212B, may be replaced by a conducting plate held at a voltage bias with respect to the remaining PM sensor (such as PM sensor 212A), the conducting plate maintained at a distance D from the sensor by a ceramic spacer 211. The details of this embodiment are explained in FIG. 3B.

Figure 3A:
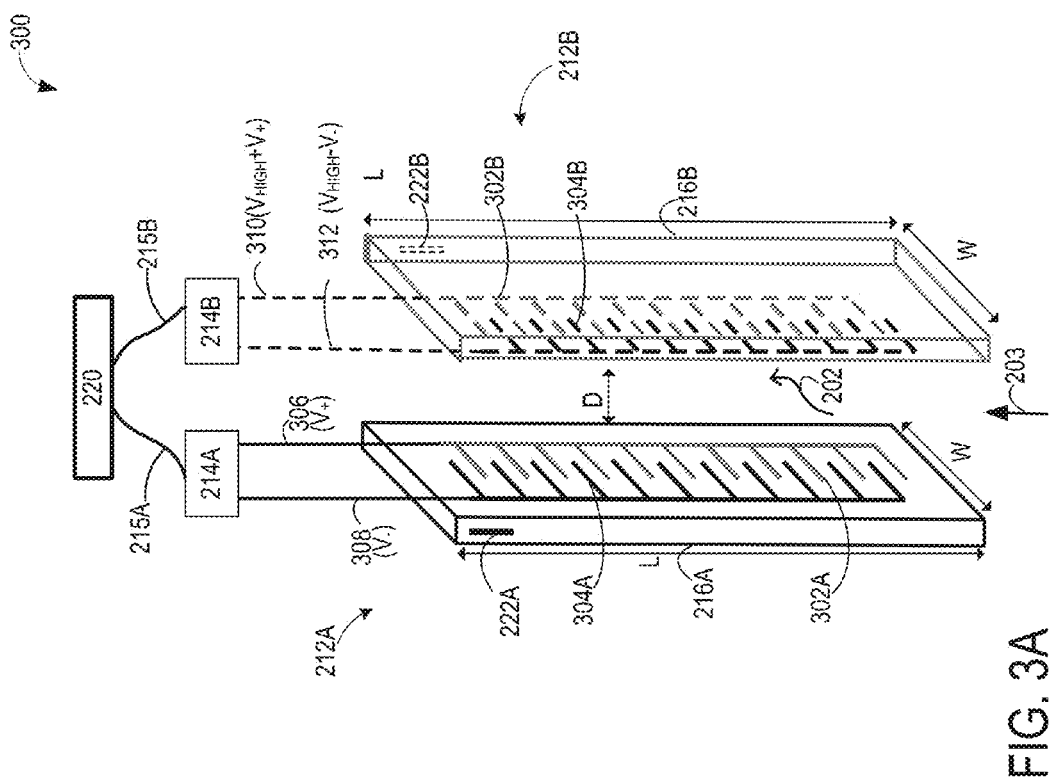

Turning now to FIG. 3A, an exploded view 300 of an example embodiment of the PM sensor assembly 204 including two PM sensors 212A and 212B is shown. The first PM sensor 212A may have interdigitated electrode pair 302A and 304A. Similarly, the second PM sensor 212B may have interdigitated electrode pair 302B and 304B. The PM sensors 212A and 212B may be mounted in the PM sensor assembly 204 such that the electrodes 302A and 304A of PM sensor 212A may be facing the corresponding electrodes 304B and 3012B of PM sensor 212B. In FIG. 3A, the electrodes 302B and 304B of PM sensor 212B are shown as dashed lines as they are not visible as depicted in this view. The comb structure of the interdigitated electrodes may cover the portion of the planar substrate 216A and 216B which is within the protection tube 206. As mentioned earlier, the spacing between the comb "tines" of the two electrodes 302A and 304A (and similarly between 302B and 304B) may typically be in the range from 10 micrometers to 100 micrometers with the linewidth of each individual "tine" of electrodes also being in the range from 10 micrometers to 100 micrometers. The number of electrode pairs of PM sensor 212A will then be given by the ratio of the total length of the electrodes (about 10 mm) divided by the average distance between adjacent "tines" of the same electrode (width of electrode 302A+width of electrode 304A+twice the gap between the electrodes 302A and 304A). In a similar way, the number of electrode pairs of PM sensor 212B may be inferred. Both the PM sensors 212A and 212B may be configured herein as planar interdigitated electrode pairs mounted in the PM sensor assembly 204 such that the first PM sensor 212A is positioned substantially parallel to the second PM sensor 212B. In addition, the sensor surface housing the interdigitated electrode pairs 302A and 304A of PM sensor 212A and the corresponding sensor surface of PM sensor 212B housing the interdigitated electrode pair 302B and 304B may face one another such that the centers of the two surfaces may be aligned with respect to one another. In other words, the sensors are not staggered but aligned such that the centers, top surfaces, bottom surfaces, and left and right sides of any one sensor correspondingly aligns with those of the other sensor. In view 300, the exhaust may flow in a direction indicated by arrow 202 between the PM sensors 212A and 212B in the PM sensor assembly 204. Alternately, the exhaust may flow in a perpendicular direction indicated by arrow 203 as explained previously. For both exhaust flow directions, the operating principle of the PM sensors is the same. The PM sensors 212A and 212B may be separated by a distance D by the ceramic spacer 211. In one example, the distance D is 2 mm. The PM sensors 212A and 212B are described in detailed in FIG. 2.

First PM sensor 212A may contain a substrate 216A having length, L, and width W, the substrate housing planar interdigitated electrodes 302A and 304A. In one example, the length of each PM sensor is 10 mm and the width of the PM sensor is 5 mm. The PM sensor 212A may also have a heating element 222A which may be used for burning PM sensor 212A free of soot particles deposited between the sensing elements 302A and 304A. One electrode of each sensor (such as electrode 302A of the first PM sensor 212A) may be coupled to a positive terminal 306 of a first voltage source in the control module 220 through the connection pad 214A and held at a positive voltage ($V_+$). The second electrode of the sensor (such as electrode 304A of the PM sensor 212A) may be coupled to a negative terminal 308 of the same voltage source in the control module 220A and held at a negative voltage ($V_-$). In this way, the two electrodes of the first sensor are held at voltages of opposite polarity (but the same absolute voltage amount) by connecting the electrodes to opposite terminals of a common voltage source. In other words, V+ and V− are of opposite polarity but the same absolute voltage. It will be appreciated that in alternate embodiments, it may be possible for the electrodes 302A and 302B to be connected to different voltage sources. For example, the electrode 302A may be connected to the positive terminal of a supply voltage of +25V or $V_+$=+25V, and the electrode 304A may be connected to ground or $V_-$=0V. The positive and negative terminals 306 and 308 may be connected to the voltage supply in the control module 220. The voltage difference applied across the terminals 306 and 308 is defined as ($V_+$−$V_-$).

As such, the details of each of the components of second PM sensor 212B may be similar to the corresponding components of PM sensor 212A described above. Second PM sensor 212B may contain a substrate 216B having length, L, and width W, the substrate housing planar interdigitated electrodes 302B and 304B. In one example, the dimensions of the second sensor may be the same as the dimensions of the first sensor. The second PM sensor 212B may also have a heating element 222B which may be used for regenerating PM sensor 212B. The first electrode 302B of the second PM sensor 212B may be coupled to the positive terminal 310 of a second voltage source in the control module 220 which is held at a voltage ($V_{HIGH}$+$V_+$) that is more positive than the positive voltage of the first electrode 302A of PM sensor 212A (that is, where $V_{HIGH}$>>$V_+$). The second electrode 304B of the PM sensor 212B may be coupled to the negative terminal 312 of the second voltage source in the control module 220B and held at a voltage ($V_{HIGH}$−$V_-$). The voltage ($V_{HIGH}$−$V_-$) applied to the electrode 304B of PM sensor 212B may be more negative compared to the negative voltage applied to the first electrode 302B of PM sensor 212B such that the voltage difference applied across the terminals 310 and 312 may be defined as: ($V_+$)−($V_-$). However, the voltage ($V_{HIGH}$−$V_-$) applied to the electrode 302B of PM sensor 212B may be more positive than the second electrode 304A of the PM sensor 212A. In other words, the second PM sensor 212B may be held at a voltage bias $V_{HIGH}$ with respect to the first PM sensor 212A By holding a voltage bias, the electrostatic attraction between any given pair of interdigitated electrodes is increased, improving their ability to catch soot. The voltages $V_{HIGH}$, $V_+$, $V_-$ may be chosen such that $V_{HIGH}$>>$V_+$>$V_-$. In one example, the values of the voltages may be $V_+$=+12.5V, $V_-$=−12.5V and $V_{HIGH}$=1000V. The voltage difference between the electrodes 302B and 304A, and similarly between 304B and 302A, generates an electric field normal to the surface of the two PM sensors thereby increasing soot capture on sensor surfaces. The operating principle and the reason behind this alignment is explained in detail in FIG. 4.

FIG. 3B shows an alternate embodiment 350 of the PM sensor assembly 204, in which the second PM sensor 212B is replaced with a conducting plate 352. In embodiment 350, the PM sensor assembly 204 comprises a first planar interdigitated electrode pair (herein PM sensor 212A) and a second conducting plate 352, separated by distance D by a ceramic spacer 211. The sensor assembly may be mounted in such a way that exhaust may flow either in the direction indicated by arrow 202 or by arrow 203 between the PM sensors 212A and the conducting plate 352 of PM sensor assembly 204 when exhaust is flowing from the particulate filter to the tailpipe. As in the configuration of FIG. 3A, the electrode 302A of the first PM sensor 212A may be coupled to a positive terminal 306 of a first voltage source in control module 220 through connection pad 214A and held at a positive voltage ($V_+$). The second electrode 304A of the PM sensor 212A may be coupled to a negative terminal 308 of the first voltage source in control module 220 through the connection pad 214A and held at a negative voltage ($V_-$). The voltage difference applied across the terminals 306 and 308 may be defined as ($V_+$)–($V_-$). The conducting plate 352 of length L and width W, may be placed at a distance D from the PM sensor 212A in the PM sensor assembly 204. In one example, the distance D is 2 mm. The conducting plate may be connected to the voltage terminal 354 through connection pad 356 and maintained at a positive potential $V_{HIGH}$ such that $V_{HIGH} \gg V_+ > V_-$. The terminals 306, 308 and 354 may be connected to the voltage supplies in the control module 220. By arranging the sensor across from a conducting plate element, an additional electric field may be generated normal to the surface of the PM sensor 212A, thereby increasing electrostatic attraction of the PMs to the sensor surface and increasing PM capture onto the sensor surface. The distance between the high voltage plate and the planar sensor element may typically be in the range 1 mm to 2 mm. The values for the magnitude of the voltage $V_{HIGH}$ and separation distance D are chosen such that the average value of the electric field E midplane between the two surfaces is approximately 1000 V/mm ($E \approx V_{HIGH}/D$).

FIG. 4 shows electric field lines generated in the example PM assembly embodiments of FIG. 3. Soot is deposited onto the PM sensor electrodes by way of electrostatic attraction of the charged soot particles to the sensor surface by the electric field generated by the planar interdigitated pair of electrodes 218A and 218B of PM sensors 212A and 212B.

In the first view 400, a cross sectional view of a single PM sensor 212A taken along a plane that is normal to the surface of the PM sensor 212A is shown. The PM sensor 212A may have substrate 216A, and interdigitated electrode pairs 302A and 304A held at positive and negative potentials via couplings to voltage terminals 306 and 308 respectively as explained in FIG. 3A. For simplicity, fewer electrode pairs 302A and 304A are shown for the PM sensor 212A in view 400. Due to the separation of the positive electrodes 302A from the negative electrodes 304A, a plurality of electric dipoles (or electric fields) may be generated along the length of the PM sensor 212A. The electric field lines, which indicate the direction of the electric field, are shown by filed lines 408 and 410. It is important to point out that the electric field lines 408 and 410 are in opposite directions, since electric field lines begin at a positive charge and end at the negative charge. In a given volume 402 of PMs or soot particles that may be electrically charged in the exhaust flowing in the direction indicated by arrow 203 (along y-axis), or in direction 202 (along z-axis), there may be a number of negatively charged particles (black dots, 404) and a number of positively charged particles (grey dots, 406). In the region very close to the surface of the electrodes 302A and 304A of PM sensor 212A, indicated by the region 414, the electric field strength may be stronger and a larger number of charged PMs may get attracted to the electrodes of opposite charge and get deposited on the surface of PM sensor 212A. In other words, negatively charged particles 404 flowing close to the PM sensor 212A will get deposited near the positive electrode 302A, while positively charged particles 406 flowing near the PM sensor 212A will be attracted to the negatively charged electrode 304A and will get deposited closer to electrode 304A. As the PMs get deposited between the electrodes 302A-304A forming soot bridges, the resistance across this electrode pair may change and this change may be detected by a circuit similar to the one shown in FIG. 5. However, the electric field strength decreases with distance according to the relation $E \sim 1/r^2$, where E is the electric field strength and r is the distance of the charged particle from the electrode surface. Hence only the particles that are very close to the electrodes 302A and 304A may experience the electric field and may get deposited on the electrodes 302A and 304. As explained above, at distances away from the electrode surface, PMs may feel negligible electric field and hence may remain undetected by the sensor. The region 412 shows particles that may not feel the electric field between the electrode pairs 302A and 304A and hence go through the PM sensor 212A undetected. The particles in region 412 may correspond to the particles that may be present in the exhaust but are not detected by the PM sensor 212A.

To improve the sensitivity of detection, and reduce the number of soot particles that go through the sensor onto the atmosphere undetected, the inventors have designed a PM sensor assembly 204 containing two sets of PM sensors 212A and 212B facing each other as shown in FIG. 3A, with an additional high voltage bias applied on PM sensor 212B with respect to the other PM sensor 212A thereby creating an additional electric field normal to both the PM sensors 212A and 212B. In an alternate embodiment shown in FIG. 3B, the PM sensor 212B may be replaced with a conducting plate 352, held at a voltage bias $V_{HIGH}$, with respect to the PM sensor 212A, again creating an additional electric field normal to both the PM sensor 212A and the conducting plate 352. By applying a voltage bias, an additional electric field is generated between the PM sensors (FIG. 3A) and the PM sensor and conducting plate (FIG. 3B). This additional electric field increases the electrostatic attraction of the charged PMs to the PM sensor surfaces and the conducting plate and improves the sensitivity of detection of the PMs by the PM sensor assembly 204.

In the cross sectional view 425 of FIG. 4, the PM sensor assembly 204 with two PM sensors 212A and 212B facing each other and separated by a distance D is shown. As described in the embodiment shown in 300, the electrode 302A of the first PM sensor 212A may be connected to a positive terminal 306 ($V_+$), the second electrode 304A of the PM sensor 212A may be connected to a negative terminal 308 ($V_-$). The electrode 302B of the second PM sensor 212B may be held at a second positive voltage 310 ($V_{HIGH}+V_+$), and the second electrode 304B of the second PM sensor 212B may be held at a voltage ($V_{HIGH}-V_-$), such that ($V_{HIGH} \gg V_+ > V_-$). In the view 425, there are two PM sensors, 212A and 212B, each having a potential difference of ($V_+-V_-$) between their individual electrodes 302A-304A and 302B-304B, and thereby generating a plurality of electric dipoles along the surface of each of the PM sensors 212A and 212B in a similar way as described in the view 400. The electric field lines are shown by 426A and 428A for PM sensor 212A, and by 426B and 428B for the PM sensor 212B, which are in opposite directions. Similarly for the PM sensor 212B, the electric field lines 426B and 428B are opposite to each other since the voltage difference between the electrodes 302B and 304B is ($V_+-V_-$).

However, there is an additional electric field generated normal to the surface of the PM sensors 212A and 212B due to the voltage bias $V_{HIGH}$ of the PM sensor 212B with respect to PM sensor 212A. For a pair of electrodes 302B-304A of PM sensor 212A and 212B, the electrode 302B is held at ($V_{HIGH}+V_+$) and the electrode 304A is held at $V_-$. An additional electric field may be generated as indicated by electric field line 430 which may act normal to the surface of the PM sensors 212A and 212B, but is in the direction from PM sensor 212B towards PM sensor 212A. For the adjacent pair of electrodes 304B-302A of PM sensors 212B and 212A, electrode 304B is held at $V_{HIGH}$-$V_-$, and the electrode 302A is held at $V_+$ and since $V_{HIGH}$>>$V_+$>$V_-$, the electrode 304B may still be at a higher potential with respect to 302A. An additional electric field may be generated normal to the surfaces of PM sensors 212A and 212B, and the direction may still be from PM sensor 212B towards PM sensor 212A, as indicated by the electric field line 432. For a region close to the surface of the PM sensors 212A and 212B, the electric field lines indicated by 426A, 428A, 426B and 428B may be strong enough to attract the PMs as described for view 400. However, due to the additional electric field lines indicated by electric field lines 430 and 432 flowing along the surface of the PM sensors 212A and 212B along the direction indicated by arrow 212, the charged PMs in the volume 402 of the exhaust may feel an additional electrostatic attraction towards the PM sensors 212A and 212B depending on their charge. In other words, the positively charged particles (grey dots, 406), may be strongly repelled by the PM sensor 212B which is held at a positive bias $V_{HIGH}$ with respect to PM sensor 212A, and hence may be strongly attracted by PM sensor 212A. Once close to the surface of the PM sensor 212A, the positively charged particles 406 will get deposited closer to the negatively charged electrode 304A as shown in the view 425. In a similar way, the negatively charged particles (black dots, 404) may be strongly attracted by the PM sensor 212B due to its voltage bias $V_{HIGH}$ with respect to the PM sensor 212A. These may then get deposited closer to the positive electrode 310 of the PM sensor 212B as shown in the view 425. The region between the two PM sensors 212A and 212B where the charged particles may experience the electrostatic attraction shown by the box 414, may cover the entire region between the two PM sensors 2121A and 212B and may be larger than the region 414 shown in view 400, where there is single PM sensor 212A.

Moreover, in view 425, as soot particles may get deposited between the electrodes 302A-304A and 302B-304B, the resistance across these electrode pairs may change and this change may be detected by a circuit shown in FIG. 5. With two PM sensors 212A and 212B facing each other, wherein one is held at a voltage bias with respect to the other, the sensitivity of the PM sensors 212A and 212B may be improved by increasing the electrostatic attraction between the two PM sensors 212A and 212B. As such, this increases the amount of soot particles deposited on the PM sensors 212A and 212B. In this embodiment, there may be two PM sensor outputs, one from each of 212A and 212B, both of which may be increased, and the average of these two sensor outputs may be used to calculate the total PMs in the engine exhaust. In one example, the average could be a statistical average or a weighted average of the outputs from both the PM sensors 212A and 212B.

Thus, it may be possible to increase the PM or soot particle detection by the two PM sensors 212A and 212B in multiple ways using the voltage bias between the sensors. As one example, by increasing $V_{HIGH}$, which is the voltage bias of PM sensor 212B with respect to PM sensor 212A, the electric field strength may be increased, which may further increase the electrostatic attraction that the charged PMs or soot particles of volume 402 may experience in the region between the two PM sensors 212A and 212B. In other words, increasing $V_{HIGH}$ may increase PM deposition on the electrodes 302A-304A and 302B-304B of the PM sensors 212A and 212B respectively. As another example, it may also be possible to increase the PM detection by decreasing the distance D between the PM sensors 212A and 212B. Decreasing the distance D between the PM sensors 212A and 212B, may increase the electric field strength between the PM sensors 212A and 212B as the magnitude of the electric field in the region between the two PM sensors is given by E≈$V_{HIGH}$/D, thereby increasing the amount of PM deposition on the PM sensors 212A and 212B. Note, E≈$V_{HIGH}$/D is the field magnitude near the midplane between the two sensors, in the region far enough away from each electrode such that the magnitude of the fields corresponding to 426A, 428A and 426B, 428B have diminished. However, the distance between the sensors may only be decreased up to a threshold corresponding to a minimum practical distance between the sensors. As one example of a practical feature to be taken into account is the acceptable tolerance on the value D required to achieve a known field value. This tolerance becomes tighter and possibly unachievable for smaller values of D. Another practical limitation is that a smaller value of D increases the probability that foreign material such a bits of metal flake from the exhaust system can short the two sensors. Higher values of D lessens this likelihood. Thus, the combination of increasing $V_{HIGH}$ and/or decreasing D can be used to maximize the electric field and hence the soot collection. This, however, has an upper limit. The dielectric break down of air will begin at electric fields near 3000 V/mm. To avoid electrical arcing between the two sensors 212A and 212B, the magnitudes of $V_{HIGH}$ and D must be chosen such that E≈$V_{HIGH}$/D must be less than ~3000 V/mm. In still a further example, where $V_{HIGH}$ may be more negative than $V_-$ but still with the constraint |$V_{HIGH}$|>>|$V_+$-$V_-$|, the electric field lines would be generated in a direction opposite to what is indicated by 430 and 432, but the two PM sensors 212A and 212B of the PM sensor assembly may still be able to detect more PMs. However, the positively charged PMs may now be detected by PM sensor 212B while negatively charged PMs may be detected by PM sensor 212A.

In the cross sectional view 450 of the sensor embodiment shown in FIG. 3B, the PM sensor 212B may be replaced with a conducting plate 352. In the view 450 of the embodiment 350, the PM sensor assembly 204 comprises of a first planar interdigitated electrode pair or PM sensor 212A and a second conducting plate 352, separated by distance D and may be mounted in such a way that the exhaust may flow in the direction indicated by arrow 202 between the PM sensors 212A and the conducting plate 352 of PM sensor assembly 204. The PM sensor 212A may have substrate 216A, and interdigitated electrode pairs 302A and 304A held at positive and negative potentials at voltage terminals 306 and 308 respectively. For simplicity, fewer electrode pairs 302A and 304A are shown for the PM sensor 212A in view 400. As explained for view 400, due to the separation of the positive electrodes 302A from the negative electrodes 304A, plurality of electric dipoles may be generated along the length of the PM sensor 212A. The electric field lines which indicate the direction of the electric field, are shown by 426A and 428A. In the absence of the conducting plate 352, the PM sensor 212A may detect the PMs in the exhaust as already described in view 400. For a single PM sensor 212A, the charged PMs may get attracted to the electrodes of opposite charge and get deposited on the surface of PM sensor 212A as described in view 400 due to the voltage difference ($V_+$-$V_-$) applied between the electrodes 302A and 304B. By placing a conducting plate 352 above the PM sensor 212A and by holding the plate 352 at a voltage bias, $V_{HIGH}$ with respect to the PM sensor 212A such that $V_{HIGH}$>>$V_+$>$V_-$, an additional electric field may be generated normal to the surface of the PM sensor 212A and the conducting plate 352. The electric field lines due to this additional electric field acting normal to the surface of the PM sensor 212A and the conducting plate 352 is shown by lines 452. Consider the same volume 402 of PMs in the exhaust, there may be negatively charged particles (black dots 404) and positively charged particles (grey dots 406). The charged particles entering the region between the conducting plate 352 and the PM sensor 426A in 450 may experience an additional stronger electric field, in addition to the local electric fields near the electrodes 426A and 428A of PM sensor 426A, due to the potential difference between the conducting plate 352 and the PM sensor 426A. The positively charged particles flowing in the region between the conducting plate 352 and PM sensor 426A, may be repelled by the conducting plate which may be held at a positive potential ($V_{HIGH}$) with respect to electrodes 302A and 304A and the positively charged particle may be attracted towards the PM sensor 212A. Once near the sensor electrodes, 302A and 304B, the positively charged particles may experience the electric field between the electrodes, and may get deposited between the electrodes 302A and 304B as shown in 450. The negatively charged particles flowing in the region between the conducting plate 352 and the PM sensor 212A, may be attracted towards the conducting plate as they exit the PM sensor assembly 204 indicated by 456. In the embodiment shown in view 450, it may be possible to capture a majority of the positively charged particles flowing between the conducting plate 352 and the PM sensor 212A, thereby increasing the sensitivity of the PM sensor 212A. It may also be possible to increase or decrease the electric field strength by varying the voltage $V_{HIGH}$, which may affect the amount of soot deposited on the PM sensor 212A since the soot deposition depends directly on the applied voltage bias $V_{HIGH}$. The voltage bias $V_{HIGH}$ of the conducting plate 352 may serve as a means to direct the positively charge soot particles toward the interdigitated electrodes of PM sensor 212A. The voltage $V_{HIGH}$ may be chosen such that the resulting electric field strength may be strong enough to push a majority of the positively charged soot particles of typical flow velocities that pass close to the high-voltage plate down to the surface of PM sensor 212A where they may be deposited, reducing the likelihood that they may escape the PM sensor 212A undetected. In an alternate configuration, it may be possible to hold the conducting plate 352 at a negative potential with respect to the PM sensor 212A in which case all the negatively charged particles may be deposited on the surface of the PM sensor 212A. Alternately, it may be possible to increase the PM detection by decreasing the distance D between the conducting plate 352 and the PM sensor 212A. Decreasing the distance D between the conducting plate 352 and the PM sensor 212A, may increase the electric field strength between the conducting plate 352 and the PM sensor 212A since E≈$V_{HIGH}$/D as explained earlier, thereby increasing the amount of PM deposition on the PM sensor 212A. Note, E≈$V_{HIGH}$/D is the field magnitude near the midplane between the sensor 212A and the conducting plate 352, in the region far enough away from the electrodes on 212A such that the magnitude of the fields corresponding to 426A and 428A have diminished.

FIG. 5 shows simple circuit diagrams for the example PM assembly embodiments, according to the present disclosure. In 500, the circuit diagram for the example PM assembly in view 300 is shown. In order to explain the circuit components, the circuits of two PM sensors 212A and 212B in view 500 are shown next to each other, however it will be appreciated that in the PM sensor assembly 204, the two PM sensors 212A and 212B are placed one above the other, separated by a distance D as described in detail in FIG. 3A. In view 500, the circuit can be partitioned into a sensing portion 502 and a controller portion 504. To simplify the circuit diagram, fewer pairs of the interdigitated electrodes 302A-304A of PM sensor 212A and the interdigitated electrodes 302B-304B of PM sensor 212B are shown. The sensing portion 502 may include the planar interdigitated electrode pair 302A-304A of the first PM sensor 212A and the planar interdigitated electrode pair 302B-304B of the second PM sensor 212B. The controller portion 504 of the PM sensor assembly 204 with the two PM sensors 212A and 212B as described in view 300, may comprise a meter or other device for measuring the impedance of the circuits connected thereto. In the exemplary controller portion 504, the impedance measurement device may include voltage sources, pull-up resistors (518, 520) and voltage measurement devices (514, 516), all of which may be housed in the control module 220 and connected to the corresponding sensors through connection pads 214A and 214B in FIG. 2, explained in detail in the following section. The example circuit described here is one example method for measuring small currents due to PM deposition on PM sensor surface. As such, there may be other ways to measure current and more complicated circuitry may be involved (op-amps for example).

The electrode 302A of the PM sensor 212A may be connected to a pull-up resistor 518 having a resistance value $R_A$ which may then be connected to the voltage terminal 306 held at a positive voltage indicated by $V_+$ by an electrically conducting lead 506. In one example, resistance value $R_A$ is 10 kΩ). Typical currents measured on existing resistive PM sensors at their maximum loading may be less than 0.1 milliamp (mA). At max current of 0.1 mA this would give a 1 V drop across $R_A$ (518). The electrode 304A of the PM sensor 212A may be connected to the voltage terminal 308 held at a negative voltage indicated by $V_-$ by an electrically conducting lead 508. Alternately, the pull-up resistor 518 may be connected between the electrode 304A and the voltage terminal 308. The terminals 306 and 308 may be connected to the positive and negative terminal of the same voltage source V which may be supplied by the control module 220 or may be connected to different voltage sources as discussed earlier. The electrode 304B of the PM sensor 212B may be connected to a pull-up resistor 520 having a resistance value $R_B$ which may then be connected to the voltage source of control module 220B by an electrically conducting lead 510 to terminal 312 held at a voltage ($V_{HIGH}-V_-$). In one example, resistance value $R_B$ is the same as resistance value $R_A$. In other examples, resistance value $R_B$ may be higher/lower than resistance value $R_A$. The electrode 302B of the PM sensor 212B may be connected to the voltage source in control module 220B by an electrically conducting lead 512 and at the terminal 310 held at a positive voltage ($V_{HIGH}+V_-$). Alternately, the pull-up resistor 520 may be connected between the electrode 302B and the voltage terminal 310. The power supplies in the control module 220 DC power sources and may be the outputs standard DC/DC converters used in automotive applications.

The terminals 306 and 308 may be chosen such that the potential difference between electrode pair 302A and 304A of the PM sensor 212A may be ($V_+-V_-$). In one example, a potential difference of 25V may be maintained. The voltages may likewise by chosen such that the potential difference between electrode pair 302B and 304B of the PM sensor 212B may also be ($V_+-V_-$), however, there may be an additional bias $V_{HIGH}$ between the PM sensors 212A and 212B as explained in view 425 which may responsible for providing an additional electric field between the two sensors as explained in FIG. 4. Between the electrically conducting leads 506 and 508, a measurement device 514 may be connected. Similarly, a measurement device 516 may be connected between the pair of conducting leads 510 and 512. The measurement device may be any device capable of reading the resistance change across the electrodes, such as a voltmeter. The voltage read by the device 514 may be $V_A$ and that by 526 may be $V_B$.

In the sensing portion 502 formed by the PM sensors 212A and 212B, the electrodes 302A, 304A, 302B and 304B may be electrically isolated, so that the resistance (or resistivity) between each pair of the PM sensors may be high in the absence of any PM between them. As PMs or soot particles get deposited between the electrodes 302A and 304A, the resistance between the electrode pair may start to decrease, implying that the voltage measured by the measurement device 514 may start decreasing. In a similar fashion, as PMs get deposited between the electrodes 302B and 304B, the resistance between the electrode pair may start to decrease, and the voltage measured by the measurement device 516 may start decreasing. The controller portion 504 may be able to determine the resistance between the electrode pairs 302A-304A and 302B-304B as a function of voltage measured by the measurement devices 514 and 516 respectively. The change in the resistance monitored by the measurement devices 514 and 516, may then be used to estimate a corresponding PM or soot load on the planar electrodes 302A-304A and 302B-304B of the two PM sensors 212A and 212B respectively. By using the collective PM output of both the PM sensors 212A and 212B, a more accurate measure of the exhaust soot load downstream of the DPF may be determined, and thereby diagnose and monitor the health and functioning of the DPF. The average value of the PM load may be based on a weighted average or a statistical average (or alternate statistical value such as mean, mode, or median value) of the output of PM sensors 212A and 212B. The estimated PM load may then be used to monitor and diagnose the exhaust DPF functioning. By increasing the sensitivity and accuracy of the PM sensors, it may be possible to detect more PMs in the exhaust, and to be able to gather a more accurate and reliable measure of the DPF soot load.

In view 550, the circuit diagram for the example PM assembly embodiment of FIG. 3B is shown. It will be appreciated that the PM sensor 212A and the conducting plate 352 are placed one above the other, separated by a distance D inside the PM sensor assembly 204 as described in detail in FIG. 3B. In view 550, the circuit may be partitioned into a sensing portion 502 and a controller portion 504. The PM sensor 212A in view 550 may include the elements described in details in view 500, and the PM sensor 212B of view 500 may be replaced by a conducting plate 352. The controller portion 504 may comprise a means for measuring the impedance of the circuits connected thereto. In the exemplary controller portion 504, the impedance measurement portion may include voltage sources, pull-up resistor (518) and voltage measurement device (514), all of which may be contained in the control module 220 in FIG. 2. The conducting plate 352 may be connected to a voltage source 552 which is held at a potential $V_{HIGH}$. Between the electrically conducting leads 506 and 508, a measurement device 514 may be connected. The measurement device 514 may be any device capable of reading the resistance change across the electrodes, such as voltmeter. The voltage read by the device 514 may be $V_A$. In the sensing portion 502 formed by the PM sensor 212A, the electrodes 302A and 304A may be electrically isolated, so that the resistance (or resistivity) between this pair may be high in the absence of any particulate matter between them. As PMs or soot particles get deposited between the electrodes 302A and 304A, the resistance between the electrode pair may start to decrease, implying that the voltage measured by the measurement device, 514 may start decreasing. The controller portion 504 may be able determine the resistance between the electrode pairs 302A-304A as a function of voltage measured by the measurement device 514. This change in the resistance monitored by the measurement devices 514, may then be converted to the PM or soot load on the planar electrodes 302A-304A of the PM sensors 212A. The average value of the PM load determined from the PM sensors 212A and 212B may then be used to This value may be more than double of what a single sensor assembly detects. The output may be further used to determine if the sensors have reached a threshold for regeneration. The regeneration process may require additional circuitry coupled to the heating elements 222A and 222B (not shown here); by raising the temperature of the heating elements, the soot particles may be removed from the surface of the sensors.

Figure 6:
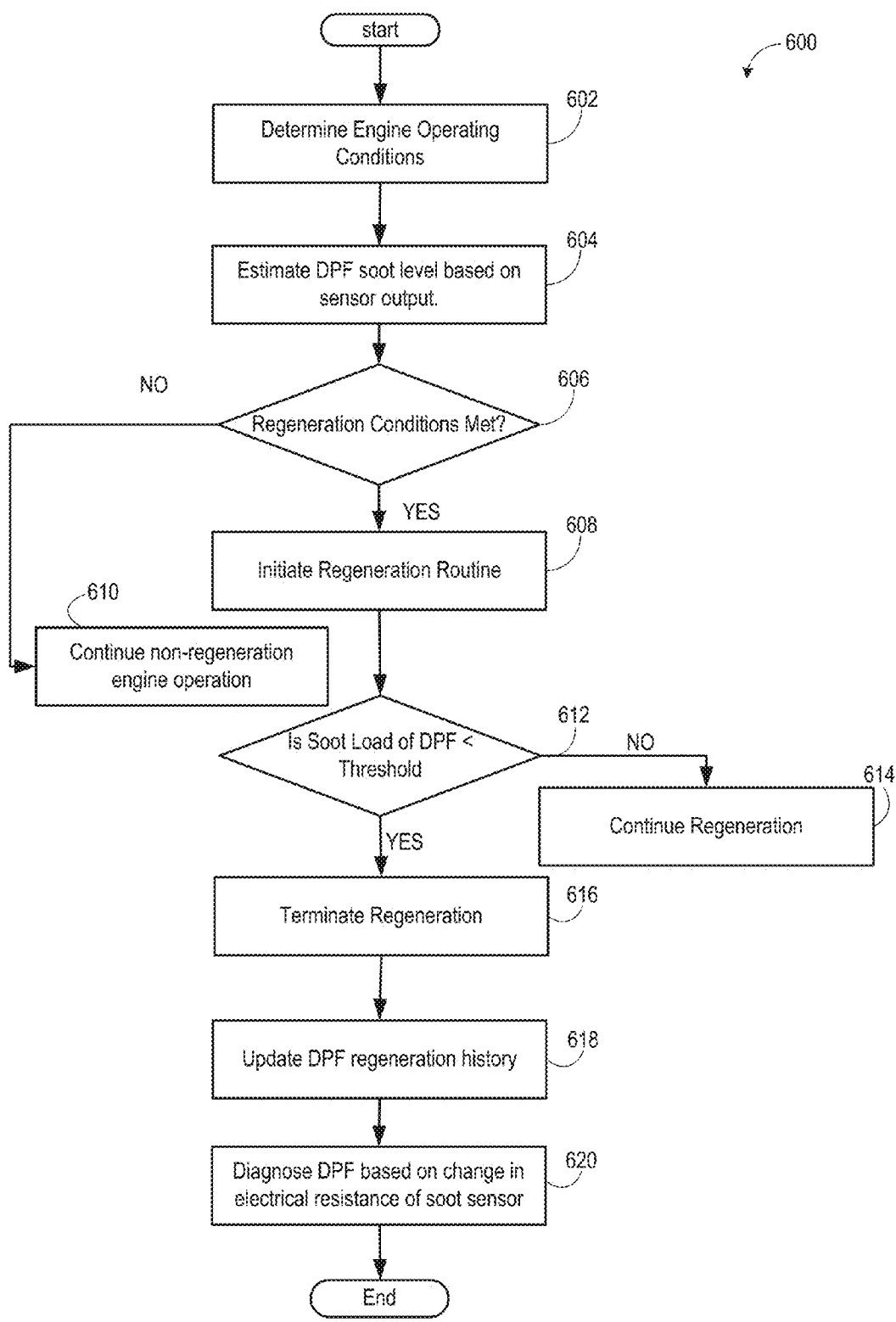
FIG. 6 shows a high level flow chart depicting a method for performing regeneration of an exhaust DPF based on the output of a pressure sensor assembly.

FIG. 6 shows a high level flow chart depicting a method for performing regeneration of an exhaust DPF based on the output of a pressure sensor assembly. Specifically, the routine uses a resistivity-based sensor regeneration process of the sensor assembly to update the soot load of the DPF and schedule regeneration of the DPF via a coupled processor.

At 602, the routine includes estimating and/or measuring engine operating conditions. Engine operating conditions determined may include, for example, engine speed, engine temperature, exhaust air-fuel ratio, exhaust temperature, duration (or distance) elapsed since a last regeneration of the DPF, boost level, ambient conditions such as barometric pressure and ambient temperature, etc.

The engine exhaust passage may include one or more pressure sensors positioned upstream and/or downstream of the DPF for determining a soot load of the DPF. For example, the engine may include a pair of pressure sensors across the DPF wherein the soot load is estimated based on the pressure difference across the DPF. In another example, the exhaust passage may include a pressure-based sensor upstream of the DPF to determine the soot load on the DPF and a resistivity based PM sensor downstream of the DPF to monitor the functioning of the DPF. The output of the pressure sensor decreases with increasing soot load and may be used to infer the soot load on the DPF. Alternately, the engine may include a resistivity-based PM sensor to monitor the soot load of the DPF wherein the resistivity-based sensor is positioned upstream of the DPF filter. It may also be possible to use a combination of the pressure sensor and resistivity-based PM sensor to determine the soot load of the DPF and diagnose the functioning of the DPF and detect degradation of the DPF (e.g., determine if the DPF is damaged or leaking), as discussed below.

At 604, the soot load on the DPF may be determined based on the output of one or more of an exhaust pressure sensor and an exhaust PM sensor assembly. Reliance on the PM sensor assembly may depend on the relative location of the PM sensors assembly with respect to the DPF. For example, the soot load may be inferred based on a change in output of the exhaust pressure sensor.

At 606, it may be determined whether filter regenerations conditions are met, for example, it may be determined whether the soot load on the DPF has reached or exceeded a threshold for regeneration. In one example, the regeneration threshold is an upper threshold above which regeneration is initiated. If no, then at 610, the engine may continue non-regeneration engine operation. If yes, then at 608 the system may adjust engine operating parameters to regenerate the DPF. The engine controller may have stored instructions to send a regeneration signal to the regeneration circuit responsive to the soot level data. During the regeneration, a temperature of the filter (or in the vicinity of the filter) may be sufficiently raised to burn off stored soot.

After regenerating the DPF, at 612, it may be determined whether the soot load is lower than a threshold. In one example, the threshold is a lower threshold below which regeneration is terminated. If the soot load is lower than the threshold, then at 616, the DPF regeneration process may be terminated. This includes discontinuing heating the filter. If the soot load of the filter is not sufficiently low, DPF regeneration may be continued at 614. At 618, the DPF regeneration history may be updated. For example, a duration elapsed between the current regeneration routine and the immediately previous regeneration routine may be determined. At 610, the DPF may be diagnosed based on the output of the PM sensor as described at FIG. 7 in the following section wherein the PM sensor is placed downstream of the DPF.

Figure 7:
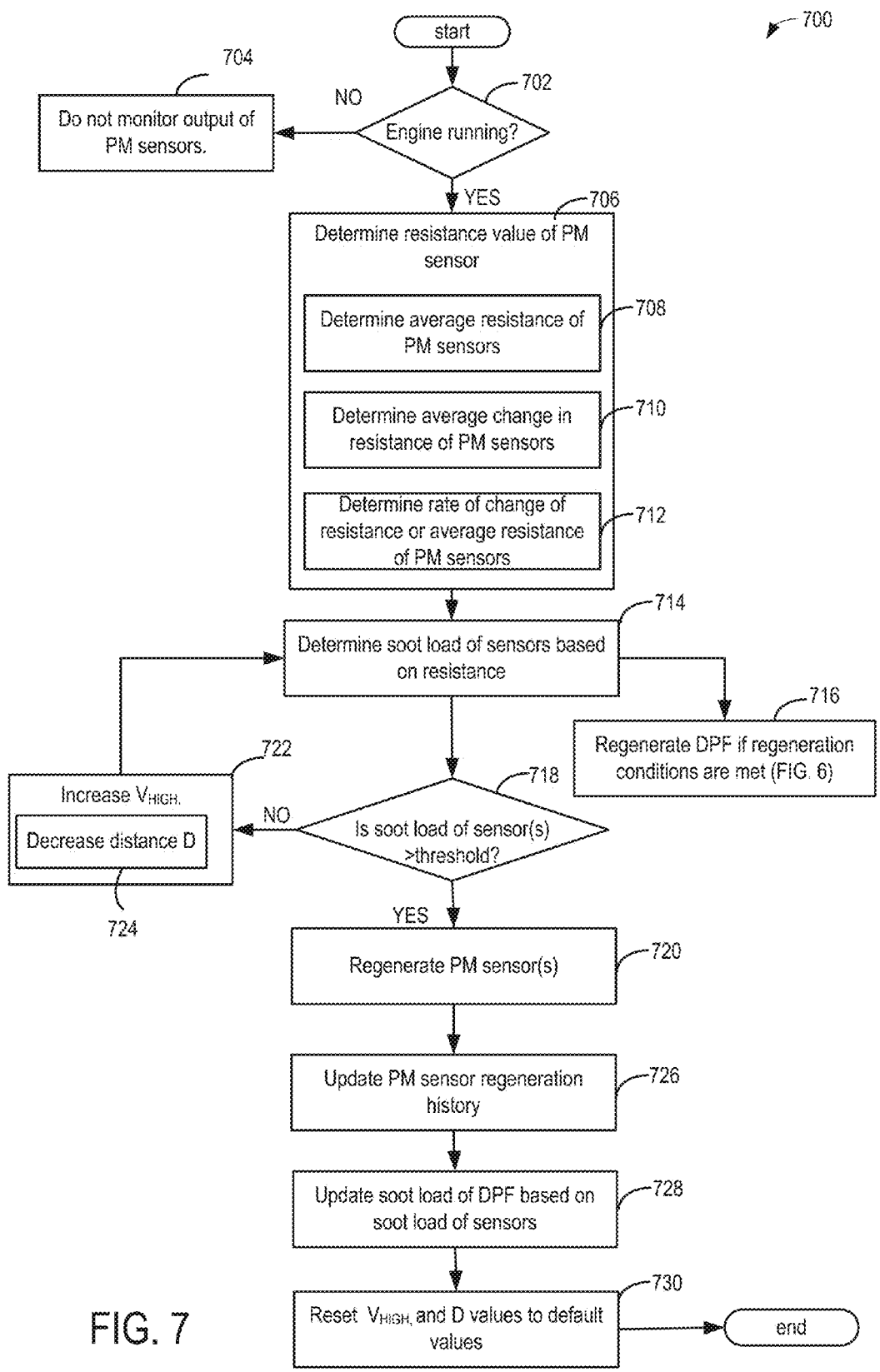
FIG. 7 shows a high level flow chart for regenerating the PM sensor assembly, according to the present disclosure.

FIG. 7 shows a high level flow chart for regenerating the PM sensor assembly 204. At 702, the routine includes confirming that the engine is running. This may be confirmed, for example, by whether the engine is undergoing combustion, rotating greater than a threshold non-zero speed, etc. If the engine is not running, at 704, the controller may be instructed not to monitor the output of the PM sensors. If the engine is running, at 706, the electrical resistance of the PM sensor 212A may be determined (in the embodiment using a single PM sensor and a conducting plate), based on the change in electrical resistance of PM sensor 212A as output by the circuit described in 550 of FIG. 5. Further, the electrical resistance may be converted to a soot load on PM sensor. In the embodiment including two PM sensors in the PM sensor assembly 204, the amount of PM in the exhaust may depend on an effective PM resistance that is based on the electrical resistance of the first pair of electrodes of PM sensor 212A, the electrical resistance of the second pair of electrodes of PM sensor 212B, the time rate of change of electrical resistance between the first pair of electrodes, and the time rate of change of electrical resistance between the second pair of electrodes in the case of PM assembly comprising of two PM sensors. These values may be determined at 708, 710 and 712 in the flow chart shown in FIG. 7 and may further be converted to the soot load on the PM sensors at 714. At 716, the DPF may be regenerated if the DPF regeneration conditions are met, as described in FIG. 6.

At 718, it may be determined if the soot load on either sensor of the PM assembly (or the single sensor of the assembly, as the case may be) is greater than the threshold for regeneration of the sensor(s). As such, when the resistance on the sensor reaches a threshold, the sensor may need to be regenerated to enable further soot to be deposited and detected. If the soot sensor load is higher than the threshold, then at 720, the PM sensors may be regenerated by heating up the sensor(s) using the heating elements 222A and 222B until the sensors are burned free of the PMs deposited on them. If the soot load is not higher, then optionally at 722, it may be determined if the detection of PMs deposited on the sensor can be increased by increasing $V_{HIGH}$. As explained in FIG. 5, increasing $V_{HIGH}$ may increase the sensitivity of detection of the PM sensor(s) by increasing the electrostatic attraction between the charged PMs and the surface of the PM sensor(s). Upon increasing $V_{HIGH}$, it may be expected that the soot load may increase, and the resistance may correspondingly also increase. Accordingly, after increasing $V_{HIGH}$, steps 714 through 718 may be repeated. Alternately, the distance D between the two PM sensors or the PM sensor and the conducting plate may be decreased to increase the sensitivity of detection at 724.

At 726, following soot sensor regeneration, the PM sensor regeneration history may be updated. For example, a frequency of soot sensor regeneration and/or an average duration between sensor regenerations may be updated. At 728, the soot load of the DPF may be updated based on the soot load on the PM sensor(s). For example, the DPF soot load may be incremented by an amount corresponding to the estimated soot load of the sensor at the time of regeneration. In other examples, each time the soot sensor is regenerated, the soot load of the DPF may be incremented by a fixed, predefined amount. At 730, the values of $V_{HIGH}$ and distance D may be reset back to default values and the routine may be terminated.

FIG. 8 illustrates an example routine 800 for diagnosing DPF functioning based on the output of the PM sensors when the PM sensor is placed downstream of the DPF. At 802, the soot load on the DPF may be determined based on the pressure sensor output. At 804, the soot load on the PM sensor assembly 204 may be determined based on the resistance changes in the PM sensors as explained in FIG. 7. At 806, it may be determined if the conditions for DPF regeneration are met (FIG. 6). If yes, then at 808, DPF regeneration may be initiated, as elaborated in FIG. 6. If not, at 810, the soot load on the DPF and the PM sensors may continue to be monitored. It may be possible to continue monitoring the PM soot load, say at time t and comparing the PM soot load at a time t with an earlier value of soot load determined at a time (t−1), for example. At 812, the PM sensor soot load at time (t) may be compared with the PM sensor soot load at an earlier time (t−1) and it may be determined if there is a significant increase in the PM soot load. If yes, then it may be indicated at 814 that the DPF is leaking. If not, at 816, it may be indicated that the DPF is not leaking and at 818, monitoring of the PM soot load and DPF soot load may be resumed. As mentioned earlier, in alternate embodiments, a PM sensor may be located downstream of the DPF. In this configuration, the PM sensor may monitor the functioning of the DPF and detect leaks in the DPF. FIG. 9 shows an example relationship between PM sensor load and DPF load when the PM sensor is located downstream of the DPF. The first plot of 900 shows the soot load on the PM sensors determined based on the resistance change across the sensors as explained in FIG. 7. The second plot shows the soot load on the DPF determined from the output of pressure sensor placed upstream to the DPF. The dashed line 902 and 904 indicate the threshold of regeneration of the PM sensor and DPF respectively.

In map 900, the line 908 indicates the soot load on the DPF which may be inferred from a pressure-based soot sensor upstream to the DPF and the curve 906 indicates the soot load on the PM sensor located downstream to the DPF.

At time t0, the DPF is relatively clean as indicated by low soot levels on the DPF, as well as the PM sensor downstream of the DPF. Over time, soot starts accumulating in the DPF and the soot load as indicated by line 908 begins to increase. During this time, since the DPF is trapping most of the soot in the exhaust, the soot detected by the downstream PM sensors is low as indicated by curve 906. At time t1, the soot load on the DPF has reached upper threshold level 904 and the DPF may be regenerated as explained in FIG. 6. Regeneration may proceed until a time t2 when the soot load of the DPF decreases below a lower threshold 906. In one example, regeneration may be commanded at t1 but may be initiated shortly thereafter. In the duration between the time regeneration is commanded and regeneration is initiated, exhaust PMs not captured on the DPF may be detected by the downstream PM sensor. However, once the regeneration of the DPF is initiated, the soot load of the downstream PM sensor may stop increasing. Thus, in response to an increase in soot load of the downstream PM sensor while the soot load of the upstream DPF is above the regeneration threshold, degradation of the DPF may not be determined and no diagnostic code may be set. Once the DPF has been regenerated, the particles in the exhaust may be trapped more efficiently and the DPF soot load may once again start to increase similar to the line 908. In this way, it may be possible to monitor the proper functioning of the DPF.

After an amount of time has passed where the soot sensor and DPF continue to operate in normal operating condition, such as at time t3, the DPF soot load based on the output of a pressure sensor placed upstream of the DPF continues to increase. At time t4, though the DPF may not have reached the threshold for regeneration, the soot load on the PM sensor may increase as indicated at 910. This indicates that there are PM particles being detected by the PM sensor placed downstream of the DPF. This increase in the soot particles detected by the PM sensor may indicate that the DPF is leaking. Thus, in response to an increase in the soot load of the downstream PM sensor while the soot load of the upstream DPF is less than the regeneration threshold, degradation of the DPF may be determined and a diagnostic code may be set. For example, an MIL may be set indicating that the DPF needs to be replaced. By virtue of the increased sensitivity of the PM sensor assembly described herein, DPF leakage may be detected in a timely manner, thereby reducing the possibility of operating the engine with a leaking particulate filter and thus reducing soot particle emission in the exhaust.

Figure 10:
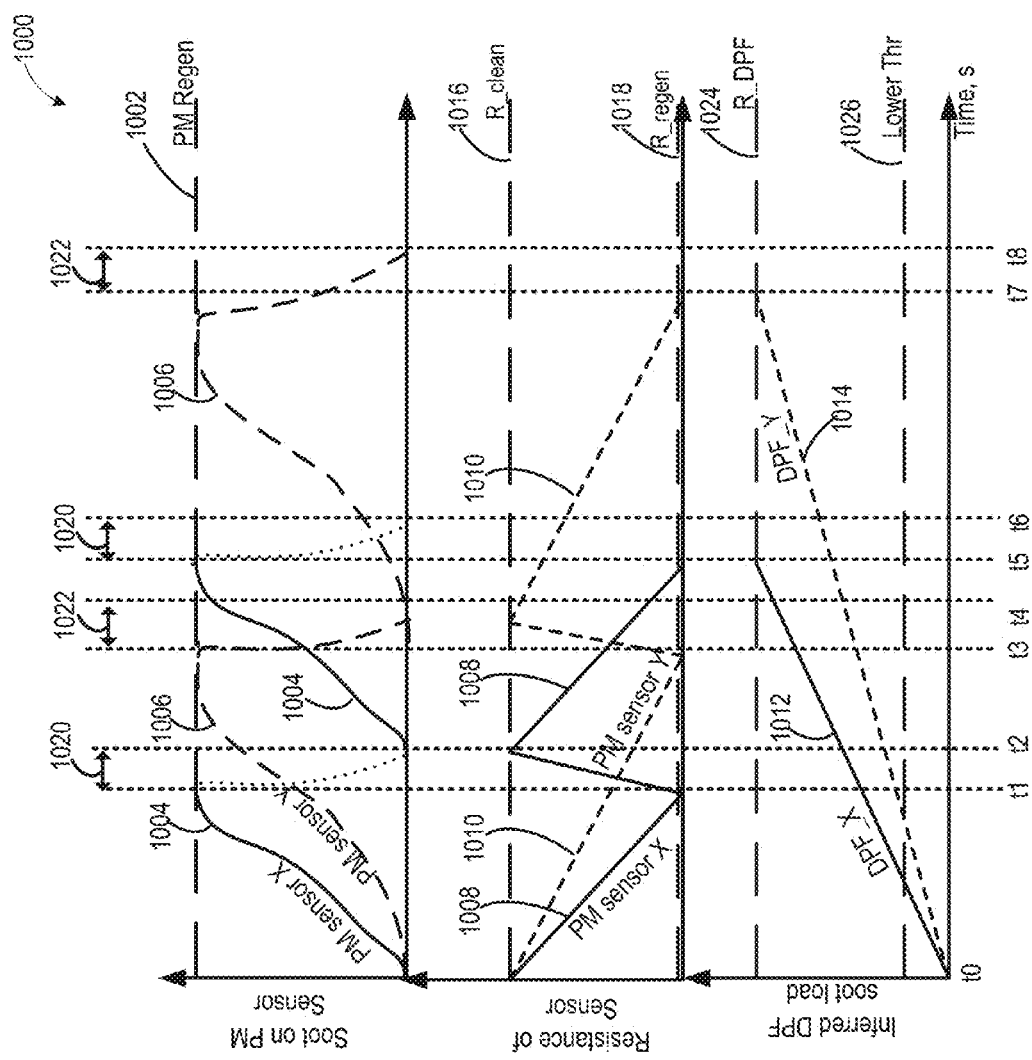
FIG. 10 shows an example relationship between PM sensor regeneration and particulate filter regeneration.

FIG. 10 shows an example relationship between PM sensor regeneration and DPF regeneration when the PM sensor is located upstream of the DPF. In this configuration, the load on the PM sensor may be used to infer the soot load on the DPF. The first plot 1000 from the top of FIG. 10 is a comparison plot between the amounts of soot deposited on a single PM sensor (such as the sensor described in embodiment 400 and a single PM sensor from the PM sensor assemblies described in embodiments 425 and 450 of FIG. 4). The dashed curve 1006 may indicate the amount of soot deposited on a single PM sensor with the interdigitated electrode pair described in embodiment 400, termed PM sensor Y for the purpose of explaining FIG. 8. The curve 804 show the total amount of PM detected by either PM sensor 212A or 212B from the PM sensor assembly described in view 300 or by the PM sensor 212A described in view 350, termed PM sensor X for the purpose of explaining FIG. 10. Horizontal line 802 corresponds to the PM sensor regeneration threshold. The X axis represents time and time increases from the left to the right side of the plot. The Y axis of plot 1000 represents the amount of soot deposited and is the lowest at the bottom of the graph and increases in magnitude towards the top of the plot.

The second plot from the top of FIG. 10 shows electrical resistance of the PM sensors X and Y. As previously described, electrical resistance of the soot sensor may decrease with increasing soot load of the PM sensor, and may increase with a decreasing soot load. Electrical resistance is at its lowest value at the bottom of the plot and increases in magnitude toward the top of the plot in the direction of the Y axis arrow. The X axis represents time and time increases from the left to the right side of the plot. Horizontal marker 1016 represents the threshold resistance of a clean PM sensor, R_clean. Horizontal marker 1018 represents the threshold resistance for PM sensor regeneration, R_regen. At resistance value R_regen, the PM sensor needs to be regenerated. These values are assumed to be the same for both PM sensor X and PM sensor Y. Solid lines 1008 indicate the change in resistance for PM sensor X, while the dashed lines 1010 correspond to the change in resistance for PM sensor Y.

The third plot from the top of FIG. 10 shows soot load of a DPF positioned upstream/downstream of PM sensors X and Y. Time starts at the left side of the plot and increases to the right. Soot load of DPF is at its lowest value at the bottom of the plot and increases toward the top of the plot in the direction of the Y axis arrow. Horizontal marker 1024 represents the upper threshold of the DPF soot load and horizontal marker 1026 represent the lower threshold of the DPF soot load in the third plot. Solid lines 1012 may indicate the inferred load of the DPF based on the output of the PM sensor X termed DPF_X, while the dashed lines 1014 may correspond to that inferred from PM sensor Y, and termed DPF_Y.

At time t0, the PM sensors X and Y are substantially clean, as indicated by sensor resistance being at a high resistance value R_clean, which corresponds to a low soot load. The PM sensor Y described in view 400, having one assembly of an interdigitated electrode pair, may have lower sensitivity due to the poor electrostatic attraction of the charged PMs at distance away from the surface of the PM sensor Y. The resistance measured across the PM sensor Y may be indicated by line 1008 and the soot load on PM sensor Y may be indicated by curve 1006. As explained in detail in FIG. 4, due to the additional electric field applied in both embodiments shown in views 425 and 450, the sensitivity of the PM sensor X may be much higher than that of PM sensor Y. Since the sensors having the additional electric field have improved sensitivity, the amount of soot detected by the PM sensor X may be larger than that detected by PM sensor Ys seen by comparing the curves 1004 and 1006. The curve 1004 of PM sensor X may reach the PM threshold 1002 faster than curve 1006 of PM sensor Y. The resistance may drop with increasing soot load on the PM sensor. As time passes, soot continues to accumulate and resistance may decrease accordingly. As a result of increased sensitivity of the sensor assembly, the resistance indicated by line 1008 of PM sensor X may decrease at a faster rate compared to the resistance indicated by line 1010 of PM sensor Y, as described in view 400. The slope of the line 1008, which corresponds to the rate of change of resistance of PM sensor X over time (dR_X/dt), may be greater than the slope of line 1010, which may correspond to the rate of change of resistance of PM sensor Y over time (dR_Y/dt).

At time t1, electrical resistance of the PM sensor X may reach a threshold for regeneration 1018 (R_regen), and regeneration of the PM sensor X may be indicated. During the time between t1 and t2, PM sensor X may be regenerated. At time t3, electrical resistance of PM sensor Y reaches the regeneration threshold 1018 (R_regen), and regeneration of the PM sensor Y may be indicated. During the time between t3 and t4, PM sensor Y may be regenerated. It is important to note that due to the increased sensitivity of the PM sensor X compared to PM sensor Y, the time to reach regeneration threshold t1 of PM sensor X may be much shorter than the time to reach regeneration threshold t3 of PM sensor Y. This may further be indicated by the slopes of lines 1008 and 1010. A processor coupled to the PM sensor may have instructions to send a regeneration signal to a regeneration circuit, responsive to the soot level data. Congruently the DPF_X and DPF_Y may be updated as described step 728 in the flow chart in FIG. 7. The soot load of DPF_X and DPF_Y continue to increase through multiple cycles of PM sensor X and Y's accumulation and regeneration. Thus, the sensor filter is regenerated more often than the particulate filter. This may indicate that the PM sensor X may be regenerated more often than the DPF, and the indication of soot level may be based on one or more of a frequency of repeatedly regenerating PM sensor X and the duration between regenerations of the PM sensor X.

After a couple of regenerations of the soot sensors, the soot load of DPF_X may have accumulated to the point of threshold 1024, R_DPF. This may signal the DPF_X to regenerate its filter, for example, by raising a filter temperature to burn off the collected particulates. The controller may have instructions for DPF regeneration based on a threshold number of soot sensor regenerations. Further, the controller may record the time in between successive soot sensor regeneration to diagnose DPF condition. However due to decreased sensitivity of PM sensor Y, the DPF_Y may not get an accurate reading of the load on the filter, and hence may be regenerated at a time point much later than its optimal regeneration condition which may lead to early degradation of DPF_Y.

In one example of an engine, the exhaust particulate filter may be regenerated in response to a voltage difference between electrodes of a first planar interdigitated electrode pair, the first electrode pair may be positioned parallel to a second planar element, the second planar element held at a voltage that is biased with relation to a voltage of at least one of the electrodes of the first pair, wherein a first major surface of the first planar pair and a second major surface of the second planar element face one another such that a center of the first major surface is aligned with a center of the second major surface. The regenerating includes initiating regeneration of the exhaust particulate filter when the voltage difference is less than a lower threshold, and terminating regeneration of the exhaust particulate filter when the voltage difference is higher than an upper threshold. The method of regeneration may include repeatedly regenerating the first electrode pair to indicate soot level responsive to the voltage difference. The indication of soot level may be based on one or more of a frequency of repeatedly regenerating the first electrode pair and a duration between regenerations of the electrode pair. The second planar element may include one of a second planar interdigitated electrode pair and a conducting plate, and holding the second planar element at a voltage that is biased includes applying a current to hold the second planar element at a voltage that is more positive than a positive voltage of a first electrode of the first pair or more negative than a negative voltage of a second electrode of the second pair.

In another example of a particulate matter sensor system may comprise of a first voltage source producing a first voltage, a first planar interdigitated electrode pair having a first electrode and a second electrode, the first electrode electrically coupled to a positive terminal of the first voltage source, the second electrode electrically coupled to a negative terminal of the first voltage source. Additionally, the particulate matter sensor may comprise a second voltage source producing a second voltage higher than the first voltage with a second planar element positioned parallel to the first planar interdigitated electrode pair and electrically coupled to the second voltage source. The second planar element is a second planar interdigitated electrode pair having a first electrode and a second electrode, the first electrode electrically coupled to a positive terminal of the second voltage source, the second electrode electrically coupled to a negative terminal of the second voltage source such that a positive voltage of the first electrode of the second planar element is more positive than a positive voltage of the first electrode of the first planar element and/or a negative voltage of the second electrode of the second planar element is more negative than a negative voltage of the second electrode of the first planar element.

In this way, by using two planar interdigitated electrode pairs or a single planar interdigitated electrode and a conducting plane in a PM sensor assembly, the technical effect of holding the second planar interdigitated electrode pair or conducting plate at a voltage bias with respect to the first interdigitated electrode pair is that the sensitivity of the particulate matter sensor is improved. Thereby, a more accurate measure of the exhaust soot load, and thereby the DPF soot load may be determined. In addition, the accuracy of detection of exhaust PMs leaking from a degraded DPF can be improved. As such, this improves the accuracy and reliability of DPF diagnostics, as well as the efficiency of filter regeneration operations. In addition, the need for extensive algorithms in the processing of PM sensor outputs is reduced. Overall, exhaust emissions compliance is improved.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an engine, comprising:
regenerating an exhaust particulate filter responsive to a voltage difference between electrodes of a first planar interdigitated electrode pair, the first electrode pair positioned parallel to a second planar element, the second planar element held at a voltage that is biased with relation to a voltage of at least one of the electrodes of the first pair, wherein a first major surface of the first planar pair and a second major surface of the second planar element face one another such that a center of the first major surface is aligned with a center of the second major surface, wherein the second planar element includes one of a second planar interdigitated electrode pair and a conducting plate, and holding the second planar element at a voltage that is biased includes applying a current to hold the second planar element at a voltage that is more positive than a positive voltage of a first electrode of the first pair or more negative than a negative voltage of a second electrode of the second pair.

2. The method of claim 1, wherein the regenerating includes initiating regeneration of the exhaust particulate filter when the voltage difference is less than a lower threshold, and terminating regeneration of the exhaust particulate filter when the voltage difference is higher than an upper threshold.

3. The method of claim 1, wherein the regenerating includes repeatedly regenerating the first electrode pair to indicate soot level responsive to the voltage difference.

4. The method of claim 3, wherein the indication of soot level is based on one or more of a frequency of repeatedly regenerating the first electrode pair and a duration between regenerations of the electrode pair.

5. The method of claim 1, further comprising updating a regeneration history after regenerating the exhaust particulate filter.

6. The method of claim 1, further comprising diagnosing the exhaust particulate filter based on a change in resistance of a soot sensor.

7. The method of claim 6, wherein the soot sensor includes the first planar interdigitated electrode pair.

8. The method of claim 6, wherein the diagnosing the exhaust particulate filter includes determining a soot load of the exhaust particulate filter based on the change in resistance of the soot sensor.

* * * * *